US006322781B1

(12) United States Patent
McCutchen

(10) Patent No.: US 6,322,781 B1
(45) Date of Patent: *Nov. 27, 2001

(54) PRODUCTION OF RECOMBINANT BACULOVIRUSES

(75) Inventor: Billy F. McCutchen, Wilmington, DE (US)

(73) Assignee: University of Maryland, College Park, College Park, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/970,264

(22) Filed: Nov. 14, 1997

Related U.S. Application Data

(63) Continuation of application No. 08/764,369, filed on Dec. 12, 1996, now abandoned.
(60) Provisional application No. 60/009,120, filed on Dec. 22, 1995.

(51) Int. Cl.[7] ........................ A61K 48/00; C12N 15/866; C12N 15/63
(52) U.S. Cl. .................... 424/93.2; 424/93.6; 435/320.1; 435/348; 435/5; 435/6; 435/455; 435/456; 435/91.4; 435/91.41
(58) Field of Search .............................. 435/69.1, 172.1, 435/172.3, 320.1, 325, 348, 5, 6, 455, 456, 91.4, 91.41; 424/93.1, 93.2, 93.6

(56) References Cited

U.S. PATENT DOCUMENTS

| | | | |
|---|---|---|---|
| 4,745,051 | 5/1988 | Smith et al. | 435/68 |
| 5,179,007 | 1/1993 | Jarvis et al. | 435/68.1 |
| 5,348,874 | 9/1994 | Savakis et al. | 435/196 |
| 5,464,758 | 11/1995 | Gossen et al. | 435/69.1 |
| 5,650,298 | 7/1997 | Bujard et al. | 435/69.7 |
| 5,654,168 | 8/1997 | Bujard et al. | 435/69.1 |
| 5,695,959 | 12/1997 | Jackson et al. | 435/69.1 |
| 5,759,809 | 6/1998 | Iatrou | 435/69.1 |
| 5,789,156 | 8/1998 | Bujard et al. | 435/6 |
| 5,814,618 | 9/1998 | Bujard et al. | 514/44 |

FOREIGN PATENT DOCUMENTS

| | | |
|---|---|---|
| 0 397 485 | 11/1990 | (EP) . |
| WO 92/05265 | 4/1992 | (WO) . |
| WO 94/00585 | 1/1994 | (WO) . |
| WO 94/28114 | 12/1994 | (WO) . |
| WO 94/29442 | 12/1994 | (WO) . |

OTHER PUBLICATIONS

Bonning, B.C., and B.D. Hammock, in Natural and Engineered Pest Management Agents, Chapter 26, pp. 368–383, 1994.*
Bonning, et al., 1992, Insect Biochemistry and Molecular Biology, vol. 22, No. 5, pp. 453–458, 1992.*
Zlotkin et al. Arch Insect Biochem Physiol 22: 55–73, 1993 (abstract only).
Thiem SM. Current Opinion in Biotechnology 1997, 8:317–322.
Hasnain et al. Gene 190: 113–118, 1997.
Vlak, J. M., Rohrmann, G. F., In Viral Insecticides for Biological Control, Maramorosch, K., Sherman, K. E., Eds., Academic Press, New York, NY. (1985), pp. 489–542.
Cartuhers, M., in Methodology of DNA and RNA Sequencing (1983), Weissman (ed.), Praeger Publishers, New York, Chapter 1.
Rubin, RA and Levy SB. Journal of Bacteriology 172:2303–2312. 1990.
Ackland–Berglund CE and Leib DA. Bio Techniques 18:196–200. 1995.
Maeda S. Curr. Opin. Biotech. Biotech. 6:313–319, 1995.
Carbonell, L. F., Klowden, M.J. Miller, L.K., J. Virol. (1985), 56, pp. 153–160.
Carbonell, L.F., Miller, L.K., Appl. Environ. Microbiol. (1987), 53, pp. 1412–1417.
Brusca, J., Summers, M., Couch, J., Courtney, L., Intervirol. (1986), 26, pp. 207–222.
Granados, R.R., Lawler, K.A., Virology (1981), 108, pp. 297–308.
O'Reilly, D.R., Miller, L.K., J. Virol. (1990), 64, pp. 1321–1328.
O'Reilly, D.R., Miller, L.K., Science (1989), 245, pp. 1110–1112.
O'Reilly, D.R., Miller, L.K., Biotechnol. (1991), 9, pp. 1086–1089.
Carbonell, L.F., Hodge, M.R., Tomalski, M.D., Miller, L.K., Gene (1988), 73, pp. 409–418.
Merryweather, A.T., Weyer, U., Harris, M.P.G., Hirst, M., Booth, T., Possee, R.D., J. Gen. Virol. (1990), 71, pp. 1535–1544.
Martens, J.W.M., Honee, G., Zuidema, D., Van Lent, J.W.M., Visser, B., Vlak, J.M., Appl. Environ. Microbiol. (1990), 56, pp. 2764–2770.
Tomalski, M.D., Miller, L.K., Nature (1991), 352, pp. 82–85.
Tomalski, M.D., Miller, L.K., Biotech. (1992), 10, pp. 545–549.
Maeda, S., Volrath, S.L., Hanzlik, T.N., Harper, S.A., Maddox, D.W., Hammock, B.D., Fowler, E., Virol. (1991), 184, pp. 777–780.
Stewart, L.M.D., Hirst, M., Ferber, M.L., Merryweather, A.T., Cayley, P.J., Possee, R.D., Nature (1991), 352, pp. 85–88.

(List continued on next page.)

Primary Examiner—David Guzo
(74) Attorney, Agent, or Firm—Sterne, Kessler, Goldstein & Fox P.L.L.C.

(57) ABSTRACT

This invention pertains to methods that facilitate production of recombinant baculoviruses that have been engineered for use as biological control agents. More specifically, this invention pertains to regulation of expression of genes encoded by recombinant baculoviruses in an insect cell or in an insect host.

27 Claims, 11 Drawing Sheets

OTHER PUBLICATIONS

Figure 1:
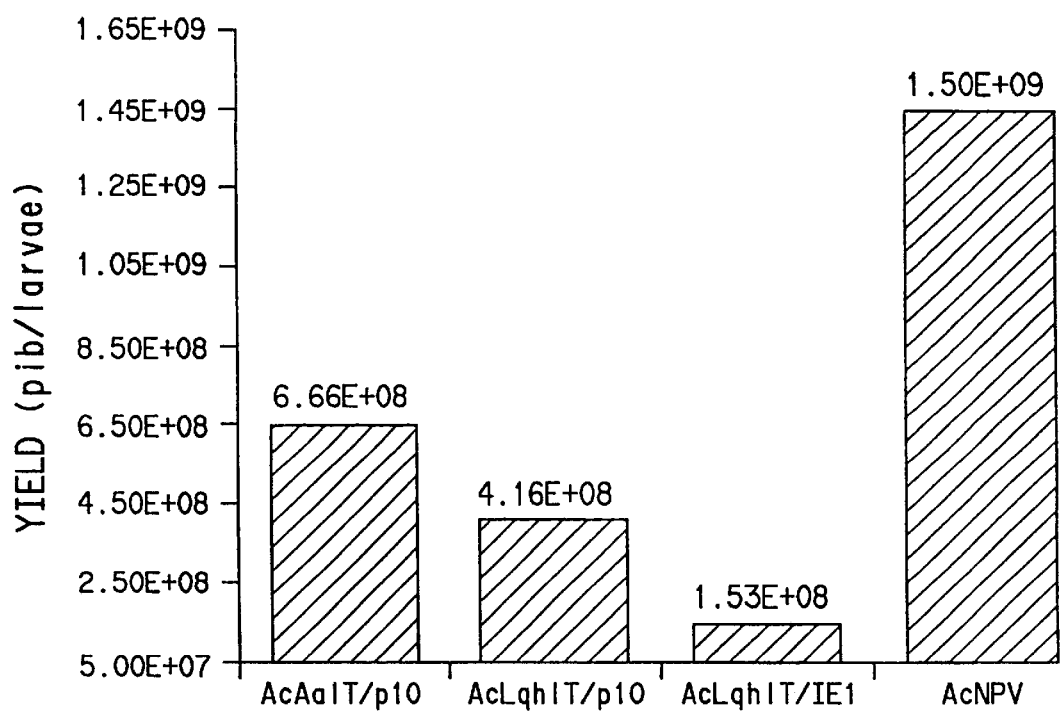

McCutchen, B.F., Choudary, P.V., Crenshaw, R., Maddox, D., Kamita, S.G., Palekar, N., Volrath, S., Fowler, E., Hammock, B.D., Maeda, S., Biotech (1991), 9, pp. 848–852.

Zlotkin, E., Phytoparasitica (1991), 19, pp. 177–182.

Walther, D., Zlotkin, E., Rathmayer, E., J. Insect Physiol. (1976), 22, pp. 1187–1194.

Zlotkin, E. in Neuropharmacology and Pesticide Action (1986), Ford, Lunt, Raey & Usherwood (eds.), Ellis Horwood, England, pp. 352–383.

Zlotkin, E., Fishman, L. Gordon, D. in Neurotox '88: Molecular Basis of Drug and Pesticide Action, (1988), Lunt (ed.), pp. 35–47.

Zlotkin, E., Rochat, H., Kupeyan, C., Miranda, F., Lissitzky, S., Biochimie (Paris) (1971), 53, pp. 1073–1078.

Lester, D., Lazarovici, P., Pelhate, M., Zlotkin, E., Biochem. Biophys. Acta. (1982), 701, pp. 370–381.

Zlotkin, E., Kaduri, D., Gordon, D., Pelhate, M., Martin, M., Rochat, H., Arch. Biochem. Biophys. (1985), 240, pp. 877–887.

Zlotkin, E., Eitan, M., Bindokas, V.P., Adams, M.E., Moyer, M., Burkhart, W., Fowler, E., Biochemistry (1991), 30, pp. 4814–4821.

Zlotkin E., Gurevitz, M., Fowler, E., Adams, M., Arch. Of Insect Biochem. Physiol. (1993), 22, pp. 55–73.

Ernst, W., Grabherr, R., Katinger, H., Nuc. Acid Res. (1994), 22, pp. 2855–2856.

Brinster, R. L., Chen, H.Y., Warren, R., Sarthy, A., Palmiter, R.D., Nature (1982), 296, pp. 39–42.

Mayo, K.E., Warren, R., Palmiter, R.D., Cell (1982), 29, pp. 99–108.

Hu, M. C.–T., Davidson, N., Cell (1987), 48, pp. 555–566.

Brown, M., Figge, J., Hansen, U., Wright, C., Jeang, K–T, Khoury, G., Livingston, D.M., Roberts, T.M., Cell (1987), 49, pp. 603–612.

Figge, J., Wright, C., Collins, C.J., Roberts, T.M., Livingston, D.M., Cell (1988), 52, pp. 713–722.

Fuerst, T.R., Fernandez, M.P., Moss, B., Proc. Natl. Acad. Sci. (1989), 86, pp. 2549–2533.

Deuschle,, U., Pepperkok, R., Wang, F., Giordano, T.J., McAllister, W.T., Ansorge, W., Bujard, H., Proc. Natl. Acad. Sci. (1989), 86, pp. 5400–5405.

Deuschle, U., Hipskind, R.A., Bujard, H., Science (1990), 248, pp. 480–483.

Labow, M.A., Baim, S.B., Shenk, T., Levine, A.J., Mol. Cell. Biol. (1990), 10, pp. 3343–3356.

Baim, S.B., Labow, M.A., Levine, A.J., Shenk, T., Proc. Natl. Acad. Sci. (1991), 88, pp. 5072–5076.

Wyborski & Short, Nucleic Acids, Res. 19, pp. 4647–4653.

Bertrand, K.P., Postle, K., Wray, L. V., Reznikoff, W.S., Gene (1983), 23, pp. 149–156.

Hillen, W., Schollmeier, K., Gatz, C., J. Mol. Biol. (1984), 172, pp. 185–201.

Gatz, C., Kaiser, A., Wendenburg, R., Mol. Gen. Genet. (1991), 227, pp. 229–237.

Wirtz, E., Clayton, C., Science (1995), 268, pp. 1179–1182.

Gossen, M., Bujard, H., Proc. Natl. Acad. Sci. (1992), 89, pp. 5547–5551.

Presnail, J.K., Hoy M.A., Proc. Natl. Acad. Sci. (1992), 89, pp. 7732–7736.

Presnail, J.K., Hoy, M.A., Exp. Applied Acarology (1994), 18, pp. 319–330.

Robertson, H.M., Nature (1993), 362, pp. 241–245.

Jeyaprakash, A., Hoy, M.A., Insect Mol. Biol. (1995), 4, pp. 31–39.

Ffrench–Constant, R.H., Mortlock, D.P., Shaffer, C.D., MacIntyre, R.J., Roush, R. T., Proc. Natl. Acad. Sci. (1991), 88, pp. 7209–7213.

Ffrench–Constant, R.H., Steichen, J.C., Ode, P.J., Pest. Bio. Phys. (1993), 46, pp. 73–77.

Passarelli, A.L., Miller, L.K., J. Virol. (1993), 67, pp. 2149–2158.

Kovacs, G.R., Choi, J., Guarino, L.A., Summers, M.D., J. Virol. (1992), 66, pp. 7429–7437.

Nissen, M.S., Friesen, P.D., J. Virol. (1989), 63, pp. 493–503.

Mevel–Ninio, M. Mariol, M., Gans, M. The EMBO Journal, (1989), 8, pp. 1549–1558.

Rubin, G.M., Spradling, A.C., Nucl. Acids Res., (1983), 11, pp. 6341–6351.

Handler, A.M., Gomez, S.P., O'Brochta, D.A., Molecular and General Genetics, (1993), 237, pp. 145–151.

O'Reilly, D.R.,et al., (1992) Baculovirus Expression Vectors: A Laboratory Manual, W.H. Freeman and Company, New York. pp. 27–46.

King, L.A., Possee, R.D., (1992) The Baulovirus Expression System: A Laboratory Guide, Chapman and Hall, London. pp. 15–36.

Johansen, J. et al., "Regulated expression at high copy number allows production of a growth–inhibiting oncogene product in Drosophila Schnieder cells," *Genes and Development* 3:882–889 (1989).

\* cited by examiner

Lq1
5' - ACGATGAATT CGGATCCTAT GAAGATCCTC CTTGCTATTG CCCTTATGCT TAGCACCGTG  60
ATGTGGGTGA GCACC - 3'  75
SEQ ID NO. 4

Lq2
5' - GACGGCTACA TCAAACGCCG CGACGGCTGC AAAGTGGCCT GCCTTATCGG C - 3'  51
SEQ ID NO. 5

Lq3
5' - AACGAGGGCT GCGACAAAGA GTGCAAAGCC TACGGGGGCA GCTACGGCTA C - 3'  51
SEQ ID NO. 6

Lq4
5' - TGCTGGACCT GGGGCCTCGC ATGCTGGTGC GAGGGCCTCC CCGACGACAA A - 3'  51
SEQ ID NO.7

Lq5
5' - ACCTGGAAAAA GCGAGACCAA CACCTGCGGC TAAGGATCCT CTAGAGTC - 3'  48
SEQ ID NO. 8

Lq6
5' - CACCCACATC ACGGTGCTAA GCATAAGGGC AATAGCAAGG AGGATCTTCA TAGGATCCGA  60
ATTCATCGT - 3'  69
SEQ ID NO. 9

Lq7
5' - AAGGCAGGCC ACTTTGCAGC CGTCGCGGCG TTTGATGTAG CCGTCGGTGC T - 3'  51
SEQ ID NO. 10

Lq8
5' - GTAGCTGCCG CCGTAGGCTT TGCACTCTTT GTCGCAGCCC TCGTTGCCGA T - 3'  51
SEQ ID NO. 11

FIG.4A

Lq9
5' - GTCGGGGAGG CCCTCGCACC AGCATGCGAG GCCCCAGGTC CAGCAGTAGC G - 3'
                                                        51
SEQ ID NO. 12

Lq10
5' - GACTCTAGAG GATCCTTAGC CGCAGGTGTT GGTCTCGCTT TTCCAGGTTT TGTC - 3'
                                                           54
SEQ ID NO. 13

FIG.4B

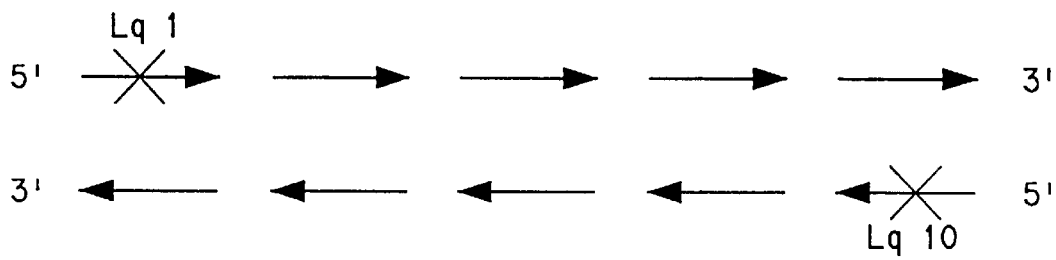
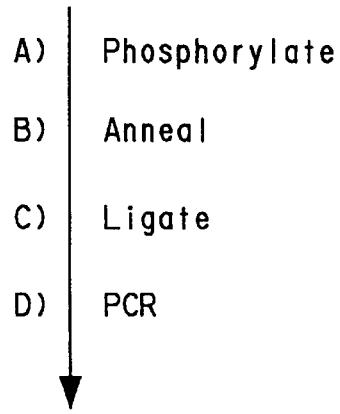
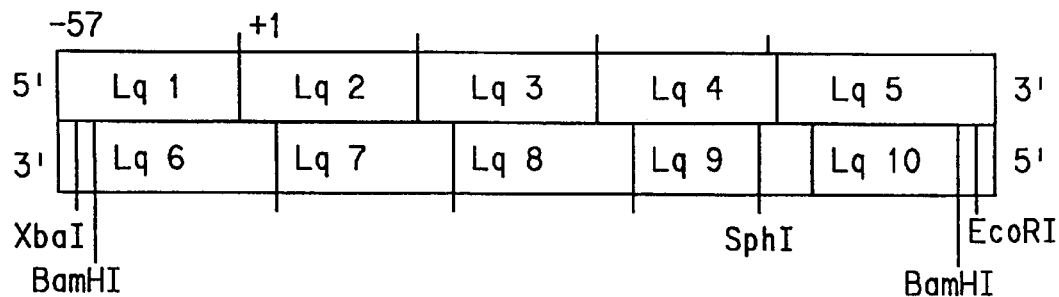
FIG.5

LqhIT Seq I.D. # 14 -> 1-phase Translation

DNA sequence   243 b.p.   atgaagatcctc ... ACCTGCGGCTAA linear

1/1 31/11
atg aag atc ctc ctt gct att gcc ctt atg ctt agc acc gtg atg tgg gtg agc acc GAC
M K I L L A I A L M L S T V M W V S T D
61/21 91/31
GGC TAC ATC AAA CGC CGC GAC GGC TGC AAA GTG GCC TGC CTT ATC GGC AAC GAG GGC TGC
G Y I K R R D G C K V A C L I G N E G C
121/41 151/51
GAC AAA GAG TGC AAG GCC TAC GGC GGC AGC TAC GGC TAC TGC TGG ACC TGG GGC CTC GCA
D K E C K A Y G G S Y G Y C W T W G L A
181/61 211/71
TGC TGG TGC GAG GGC CTC CCC GAC GAC AAA ACC TGG AAA AGC GAA ACC AAC ACC TGC GGC
C W C E G L P D D K T W K S E T N T C G
241/81
TAA
*

FIG.6

TETRIE1A

```
  1  msrldkskvl nsalellnev giegltttrkl aqklgveqpt lywhvknkra
 51  lldalaleml drhhthfcpl egeswqdflr nnaksfrcal lshrdgakvh
101  lgtrptekqy etlenqlafl cqqgfslena lyalsavghf tlgcvledqe
151  hqvakeeret pttdsmppll rqaielfdhq gaepaflfgl eliicglekq
201  lkcesgsrsM TQINFNASYT SASTPSRASF DNSYSEFCDK QPNDYLSYYN
251  HPTPDGADTV ISDSETAARS NFLASVNSLT DNDLVECLLK TTDNLEEAVS
301  SAYYSESLEQ PVVEQPSPSS AYHAESFEHS AGVNQPSATG TKRKLDEYLD
351  NSQG*  SEQ. ID NO. 21
```

FIG. 8

PRODUCTION OF RECOMBINANT BACULOVIRUSES

This is a continuation, of application Ser. No. 08/764,369 filed Dec. 12, 1996, now abandoned and this application also claims priority to provisional application No. 60/009,120, filed Dec. 22, 1995.

BACKGROUND OF THE INVENTION

Chemical insecticides are an integral component of modern agriculture, and are an effective means for reducing crop damage by controlling insect pests. However, chemical agents are under continuous scrutiny due to the potential for environmental contamination, selection of resistant populations of agronomic pests, and toxicity to non-target organisms such as beneficial insects, aquatic organisms, animals and man. As a result, alternative strategies for insect control are being sought that are effective and yet benign to non-target populations and the environment.

One of these strategies is to use microorganisms that are naturally occurring pathogens of target insect populations. However, many candidate entomopathogens that would be promising insect control agents lack the properties of classical chemical insecticides such as host-specificity and rapid action that farmers and others in agribusiness have grown accustomed to. Viruses from the family Baculoviridae are host-specific and have inert environmental properties, but lack the ability to rapidly neutralize a target population before significant crop damage takes place. Fortunately, modern molecular biology provides the tools to produce recombinant baculoviruses engineered for use as biological control agents.

An attractive attribute of baculoviruses is their narrow host specificity. These viruses infect only arthropods and possess relatively narrow host ranges even within a particular insect order. Host specificity has been examined by electron microscopy, DNA hybridization and recombinant DNA technology (References 1–3). These studies indicate that the narrow host range is due, at least in part, to the inability of baculoviruses to transfer viral DNA into the mammalian cell nucleus.

Baculoviruses are divided into three subfamilies, including non-occluded baculoviruses (NOVs), granulosis viruses (GVs) and nuclear polyhedrosis viruses (NPVs). Although certain GVs and NOVs have been carefully studied, NPVs are the most thoroughly characterized of the baculovirus subfamilies. Examples of NPVs include *Autographa californica* NPV, *Spodoptera exigua* NPV, *Heliothis armigera* NPV, *Helicoverpa zea* NPV, *Spodoptera frugiperda* NPV, *Trichoplusia ni* NPV, *Mamestra brassicae* NPV, *Lymantria dispar* NPV, *Spodoptera litturalis* NPV, *Syngrapha facifera* NPV, *Choristoneura fumiferana* NPV, *Anticarsia gemmatalis* NPV, and *Heliothis virescens* NPV.

Due in part to the availability of efficient cell culture systems and facile cloning vectors, NPVs have been used as eukaryotic expression vectors to synthesize desirable heterologous proteins (4,5). One virus in particular, *Autographa californica* NPV (AcNPV), is the accepted model virus for introduction and expression of heterologous genes in baculovirus expression systems. Although this virus is routinely used as an important in vitro means of providing for high yields of recombinant proteins in a eukaryotic expression system, thus affording appropriate post-translational modification of expressed proteins, AcNPV is capable of infecting many families of Lepidopteran insects that are important economic pests.

In spite of the potential practical advantages of baculovirus-based pest control agents, a variety of disadvantages have curtailed their use in modem agriculture. The most significant barrier to more widespread use of these viruses in row-crop agriculture is the significant time delay between their application and effective control of crop damage caused by the host insects. Unlike the rapid effects observed upon application of classical chemical insecticides, significant wild-type baculovirus-mediated insect control occurs only after in vivo populations of virus have reached levels high enough to compromise host activity. This may occur as long as several weeks after infection in a cycle that involves two types of virions. Following infection of insect cells, budded virions (BVs or extracellular virus, ECV) are produced upon movement of nucleocapsids to the plasma membrane. These virions shed their nuclear-derived coat in the cytoplasm and bud through the cytoplasmic membrane into the hemocoel of the insect host. This process leads to systemic infection of the host insect. Later in the infection process, virions become occluded (occluded virions) by a protein matrix consisting substantially of the polyhedrin protein, thus forming polyhedral inclusion bodies (PIBs or occlusion bodies, OBs). These inclusion bodies are the orally infectious form of the virus and provide for horizontal transmission of the virus between insect hosts (6,7). Uninfected larvae feed on virus-contaminated substrates and ingest PIBs. The proteinaceous matrix is solubilized by the action of the basic pH of the insect midgut found in many lepidopterous larvae. The liberated virion nucleocapsids, containing the viral DNA genome, attach to and infect the epithelial cells of the larval midgut. Typically, the infected insect will continue to develop and consume plant material while the virus exponentially propagates within the host. Eventually, often after several weeks or longer have passed, the infected larvae will become fully involved and expire.

Through the use of recombinant DNA technology, NPVs have been genetically engineered to increase their rate of insect killing by either the introduction of genes directing the expression of insecticidal proteins or the deletion of genes from the viral genome (8–10). Both strategies yield biological insecticides that display more rapid insect control than wild-type, unengineered NPVs. The most effective recombinant NPVs have been engineered to express insect-selective neurotoxins (11–18). The expressed toxins accelerate the onset of cytotoxicity, resulting in more rapid insect control. These recombinant viruses kill their hosts in 20–30% less time than wild-type NPVs.

Baculoviruses destined for use as biological pest control agents must be produced in large quantities. Mass-production of virus can be accomplished with standard in vitro insect cell culture systems or by in vivo production in infected insect larvae. Yields of viral particles in either system are dependent on sufficient viral replication, which is in turn dependent on maintenance of healthy cells or insects. Premature cell cytotoxicity or insect death will necessarily limit viral replication, thereby reducing the number of progeny virus produced.

Genetically modified baculoviruses, engineered to more rapidly neutralize target insects, may also result in less viral replication and result in lower yields of viral progeny per infected cell (in vitro) or per infected insect (in vivo). Thus, the means used to improve the efficacy of baculovirus-mediated insect control agents, making them viable alternatives or adjuncts to traditional chemical insecticides, may in fact defeat the economic viability of this pest control strategy. Accordingly, a method for efficient production of insecticidal baculoviruses is needed that overcomes the barrier of premature cytotoxicity or premature killing of the host cell or insect.

SUMMARY OF THE INVENTION

This invention pertains to methods that facilitate production of recombinant baculoviruses that have been engineered for use as biological control agents. More specifically, this invention pertains to regulation of expression of genes encoded by recombinant baculoviruses in an insect cell or in an insect host.

In one embodiment, this invention pertains to a method for controlling expression of a gene encoded by the genome of a recombinant baculovirus in insect cell culture or in viable insects wherein said insect cells or insects have been genetically engineered to express a protein that regulates expression of a gene encoded by the baculovirus genome.

More particularly, the method for controlling expression of an insecticidal protein encoded by a chimeric gene in the genome of a recombinant baculovirus can be exploited for efficient production of recombinant insecticidal baculoviruses in insect cell culture or in viable insects, the steps of said method comprising:

(a) constructing a recombinant insect cell having a first chimeric gene comprising a first nucleic acid fragment encoding a first promoter, the first nucleic acid fragment operably linked to a second nucleic acid fragment encoding a regulatory protein capable of affecting gene expression;

(b) constructing a recombinant baculovirus expression vector having a second chimeric gene comprising a third nucleic acid fragment encoding a second promoter that is affected by the regulatory protein of step (a), said third nucleic acid fragment operably linked to a fourth nucleic acid fragment that encodes an insecticidal protein;

(c) introducing the recombinant baculovirus expression vector of (b) stably into the recombinant insect cell of (a); and (d) maintaining the recombinant insect cell of (a) containing the recombinant baculovirus expression vector of (b) under conditions that support baculoviral replication;

wherein expression of the regulatory protein of step (a) affects expression of the insecticidal protein of step (b).

In another embodiment, this invention pertains to a method for controlling expression of an insecticidal protein encoded by a chimeric gene present in the genome of a recombinant baculovirus comprising:

(a) constructing a recombinant insect cell having a first chimeric gene comprising a first nucleic acid fragment encoding a first promoter, the first nucleic acid fragment operably linked to a second nucleic acid fragment encoding a regulatory protein capable of affecting gene expression;

(b) constructing a recombinant baculovirus expression vector having a second chimeric gene comprising a third nucleic acid fragment encoding a second promoter that is affected by the regulatory protein of step (a), said third nucleic acid fragment operably linked to a fourth nucleic acid fragment encoding an insecticidal protein;

(c) introducing the recombinant baculovirus expression vector of (b) into the recombinant insect cell of (a); and (d) maintaining the recombinant insect cell of (a) containing the recombinant baculovirus expression vector of (b) under conditions that support baculoviral replication wherein expression of the regulatory protein of step (a) affects expression of the insecticidal protein of step (b).

In another embodiment, this invention pertains to a method for controlling expression of an insecticidal protein encoded by a chimeric gene present in the genome of a recombinant baculovirus comprising:

(a) constructing a recombinant baculovirus expression vector having (1) a first chimeric gene comprising a first nucleic acid fragment encoding a first promoter, the first nucleic acid fragment operably linked to a second nucleic acid fragment encoding a regulatory protein capable of affecting gene expression and (2) a second chimeric gene comprising a third nucleic acid fragment encoding a second promoter that is affected by said regulatory protein, said third nucleic acid fragment operably linked to a fourth nucleic acid fragment encoding an insecticidal protein;

(b) introducing the recombinant baculovirus expression vector of (a) into an insect cell; and (c) maintaining the insect cell of (b) under conditions that support baculoviral replication wherein expression of said regulatory protein affects expression of said insecticidal protein.

In another embodiment, this invention pertains to a method for the production of insecticidal recombinant baculoviruses comprising:

(a) constructing a recombinant insect cell having a first chimeric gene comprising a first nucleic acid fragment encoding a first promoter, the first nucleic acid fragment operably linked to a second nucleic acid fragment encoding a regulatory protein capable of affecting gene expression;

(b) constructing a recombinant baculovirus expression vector having a second chimeric gene comprising a third nucleic acid fragment encoding a second promoter that is affected by the regulatory protein of step (a), said third nucleic acid fragment operably linked to a fourth nucleic acid fragment encoding an insecticidal protein;

(c) introducing the recombinant baculovirus expression vector of (b) into the recombinant insect cell of (a);

(d) maintaining the recombinant insect cell of (a) containing the recombinant baculovirus expression vector of (b) under conditions that support baculoviral replication wherein expression of the regulatory protein of step (a) affects expression of the insecticidal protein of step (b); and (e) collecting progeny viruses.

In another embodiment, this invention pertains to a method for the production of insecticidal recombinant baculoviruses comprising:

(a) constructing a recombinant baculovirus expression vector having (1) a first chimeric gene comprising a first nucleic acid fragment encoding a first promoter, the first nucleic acid fragment operably linked to a second nucleic acid fragment encoding a regulatory protein capable of affecting gene expression and (2) a second chimeric gene comprising a third nucleic acid fragment encoding a second promoter that is affected by said regulatory protein, said third nucleic acid fragment operably linked to a fourth nucleic acid fragment encoding an insecticidal protein;

(b) introducing the recombinant baculovirus expression vector of (a) into an insect cell;

(c) maintaining the insect cell of (b) under conditions that support baculoviral replication wherein expression of said regulatory protein affects expression of said insecticidal protein; and (d) collecting progeny viruses.

In another embodiment, this invention pertains to methods for the production of insecticidal recombinant baculoviruses wherein the insect cell containing the recombinant baculovirus expression vector is maintained in an in vitro cell culture.

In another embodiment, this invention pertains to the methods for the production of insecticidal recombinant baculoviruses wherein the insect cell containing the recombinant baculovirus expression vector is maintained within an intact, living insect.

In another embodiment, this invention pertains to a method for the production of insecticidal recombinant baculoviruses comprising:

(a) constructing a recombinant baculovirus expression vector having (1) a first chimeric gene comprising a first nucleic acid fragment encoding a first promoter, the first nucleic acid fragment operably linked to a second nucleic acid fragment encoding a tetracycline transactivator protein and (2) a second chimeric gene comprising a third nucleic acid fragment encoding one or more tetracycline operator sites operably linked to a minimal promoter sequence, said third nucleic acid fragment operably linked to a fourth nucleic acid fragment encoding an insect-selective neurotoxin;

(b) introducing the recombinant baculovirus expression vector of (a) into an insect cell;

(c) maintaining the insect cell of (b) in the presence of an effective amount of tetracycline or a tetracycline analog such that the tetracycline transactivator protein is unable to bind to the tetracycline operator sites present on said third nucleic acid fragment and thereby unable to induce gene expression directed by the minimal promoter sequence operably linked to said operator sites; and (d) collecting progeny viruses.

In another embodiment, this invention pertains to a recombinant insect cell containing a chimeric gene comprising a first nucleic acid fragment encoding a first promoter, the first nucleic acid fragment operably linked to a second nucleic acid fragment encoding a regulatory protein capable of affecting gene expression directed by a second promoter.

In another embodiment, this invention pertains to a transgenic insect comprising one or more recombinant insect cells containing a chimeric gene comprising a first nucleic acid fragment encoding a first promoter, the first nucleic acid fragment operably linked to a second nucleic acid fragment encoding a regulatory protein capable of affecting gene expression directed by a second promoter.

In another embodiment, this invention pertains to an insect cell or a transgenic insect comprising one or more recombinant insect cells, said insect cells containing a chimeric gene comprising a first nucleic acid fragment encoding a first promoter, the first nucleic acid fragment operably linked to a second nucleic acid fragment encoding a regulatory protein capable of affecting gene expression directed by a second promoter, wherein the regulatory protein is the tetracycline transactivator protein.

In another embodiment, this invention pertains to a recombinant baculovirus expression vector having a first chimeric gene comprising a first nucleic acid fragment encoding a first promoter operably linked to a second nucleic acid fragment encoding an insecticidal protein, said first promoter affected by a regulatory protein expressed by a recombinant insect cell having a second chimeric gene comprising a third nucleic acid fragment encoding a second promoter, the third nucleic acid fragment operably linked to a fourth nucleic acid fragment encoding said regulatory protein.

In another embodiment, this invention pertains to a recombinant baculovirus expression vector having a first chimeric gene comprising a first nucleic acid fragment encoding a first promoter operably linked to a second nucleic acid fragment encoding an insecticidal protein, said first promoter affected by a regulatory protein expressed by a recombinant insect cell having a second chimeric gene comprising a third nucleic acid fragment encoding a second promoter, the third nucleic acid fragment operably linked to a fourth nucleic acid fragment encoding said regulatory protein, wherein said first nucleic acid fragment comprises one or more tetracycline operator sites operably linked to a minimal promoter.

In another embodiment, this invention pertains to a recombinant baculovirus expression vector having (1) a first chimeric gene comprising a first nucleic acid fragment encoding a first promoter, the first nucleic acid fragment operably linked to a second nucleic acid fragment encoding a regulatory protein capable of affecting gene expression and (2) having a second chimeric gene comprising a third nucleic acid fragment encoding a second promoter that is affected by said regulatory protein, said third nucleic acid fragment operably linked to a fourth nucleic acid fragment encoding an insecticidal protein.

In another embodiment, this invention pertains to a recombinant baculovirus expression vector having (1) a first chimeric gene comprising a first nucleic acid fragment encoding a first promoter, the first nucleic acid fragment operably linked to a second nucleic acid fragment encoding a regulatory protein capable of affecting gene expression and (2) having a second chimeric gene comprising a third nucleic acid fragment encoding a second promoter that is affected by said regulatory protein, said third nucleic acid fragment operably linked to a fourth nucleic acid fragment encoding an insecticidal protein, wherein said regulatory protein is a tetracycline transactivator protein and wherein said third nucleic acid fragment comprises one or more tetracycline operator sites operably linked to a minimal promoter.

BRIEF DESCRIPTION OF THE DRAWINGS AND SEQUENCE LISTINGS

FIG. 1. Quantification of recombinant and wild-type viral progeny as polyhedrin inclusion bodies (PIBs) from larvae of H. virescens. "AcAaIT/p10" represents recombinant baculoviruses wherein expression of AaIT toxin is controlled by the late baculoviral p10 promoter. "AcLqhIT/p10" represents recombinant baculoviruses wherein expression of LqhIT2 toxin is controlled by the very late baculoviral p10 promoter. "AcLqhIT/IE1" represents recombinant baculoviruses wherein expression of LqhIT2 toxin is controlled by the early baculoviral IE1 promoter. "AcNPV" represents wild-type vaculovirus.

Figure 2:
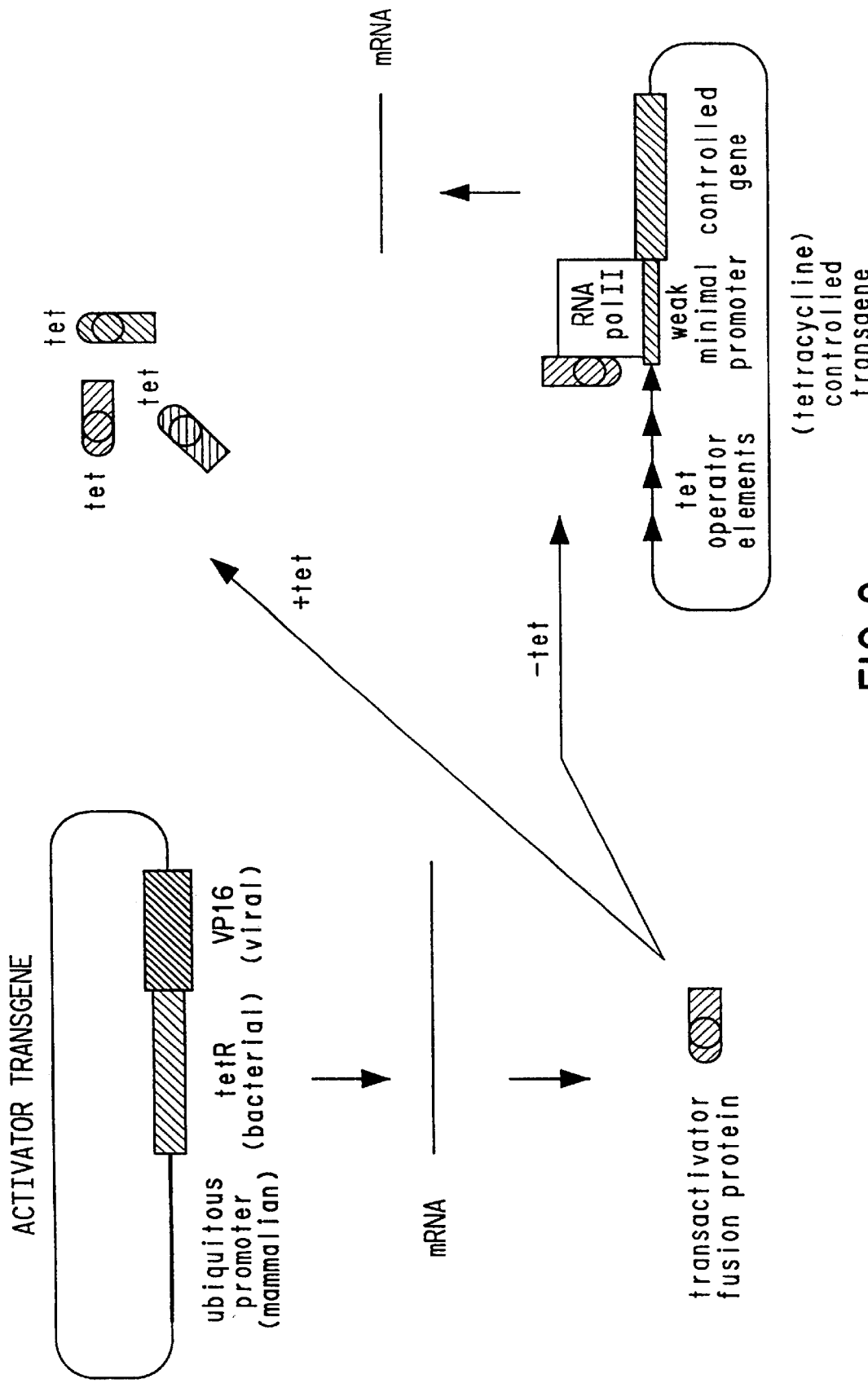

FIG. 2. Schematic representation of a tetracycline transactivator controllable system.

Figure 3:
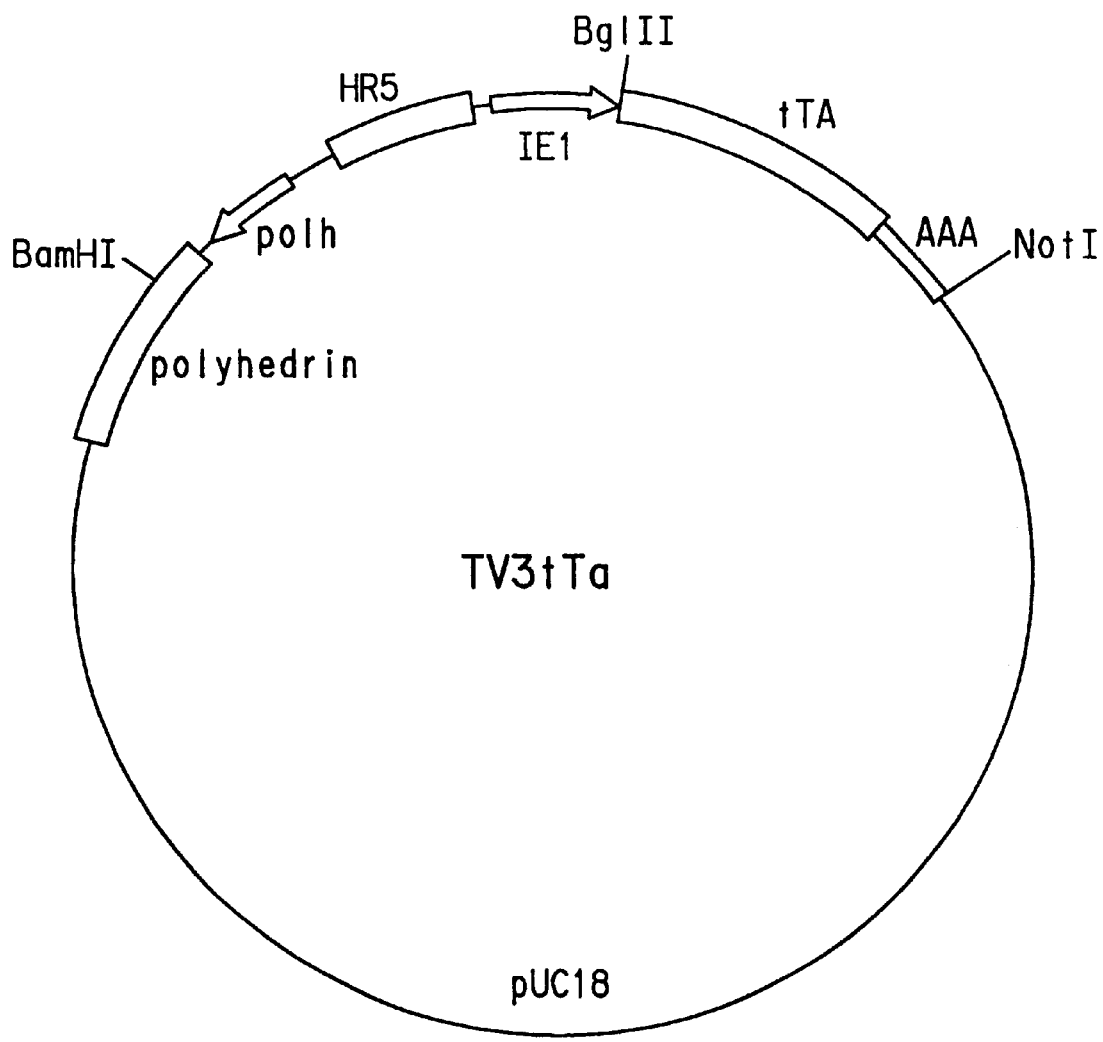

FIG. 3. Plasmid map of TV3tTa.

FIGS. 4A and 4B. Sequence of the synthetic oligonucleotides used to construct the LqhIT2 gene. Oligonucleotide Lq1 (SEQ ID NO:4) encodes the Bombyxin signal peptide. Oligonucleotides Lq1 (SEQ ID NO:4) and Lq10 (SEQ ID NO:13) were used as primers for PCR amplification of the synthetic gene.

FIG. 5. Diagramatic representation of the strategy used to prepare the LqhIT2 gene. Oligonucleotides Lq1 (SEQ ID NO:4) and Lq10 (SEQ ID NO:13) (marked with an "X") served as amplification primers for PCR reactions. Unique restriction enzyme cleavage sites are indicated.

FIG. 6. Nucleotide (SEQ ID NO:14) and corresponding amino acid sequences of the LqhIT2 gene. Lower case letters in the nucleotide sequence (nucleotides 1–57, encoding amino acids 1–19) indicate nucleotides encoding the Bombyxin signal peptide.

Figure 7:
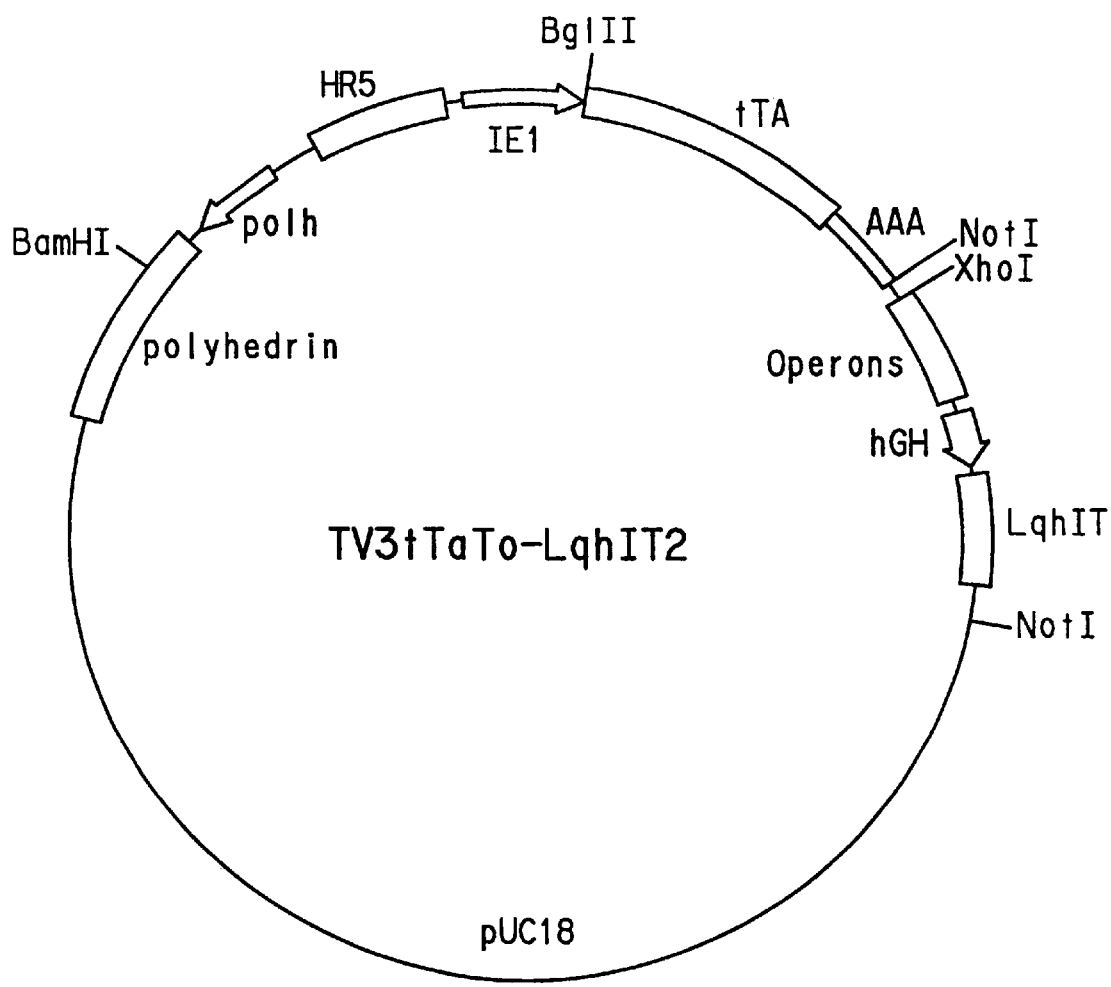

FIG. 7. Map of the baculovirus expression vector TV3tTaTo-LqhIT2.

FIG. 8. Amino acid sequence (SEQ ID NO:21) of tetrIE1A. The tetR and IE1A regions of the transactivator are indicated by lower case and capital letters, respectively. The two amino acids residue indicated in bold (positions 208 and 209) have been added on as a result of extra restriction sites present in the sequence used to facilitate the in-frame insertion of tetR and IE1A.

Figure 9:
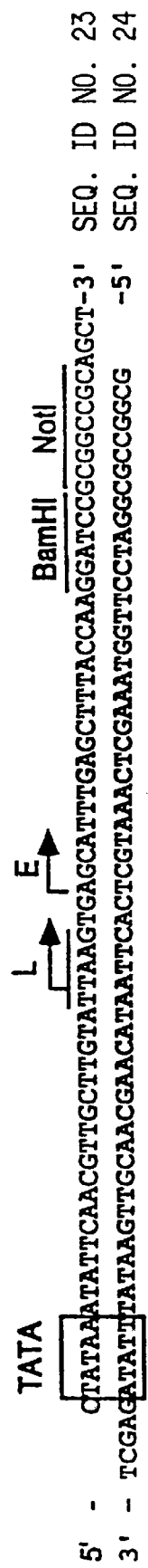

FIG. 9. Nucleotide sequences (SEQ ID NO:23 and 24) of the minimal p35 gene promoter of AcMNPV identifying the positions of the TATA box, and the early (E) and late (L) transcriptional start sites. Restriction sites to be used for future insertion of foreign genes are also indicated.

Figure 10:
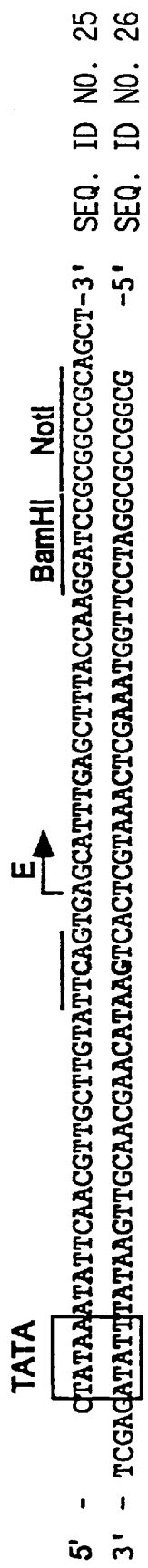

FIG. 10. Nucleotide sequences (SEQ ID NO:25 and 26) of the modified minimal p35 gene promoter of AcMNPV identifying the positions of the TATA box, and the early (E) and late (L) transcriptional start sites. The single base-pair mutation in p35m is indicated in bold. Restriction sites to be used for future insertion of foreign genes are also indicated.

FIG. 11. Diagram of the region immediately upstream of the polyhedrin gene in transfer vectors pTV3(M)lq+ and pTV3(M)lq−. The relative positions of the transactivator gene and a cassette containing tet operator sequences upstream of the p35/p35m minimal promoter and LqhIT are indicated.

FIG. 12. Diagram of the region immediately upstream of the polyhedrin gene in transfer vectors ptTA(M)lq+ and ptTA(M)lq−. The relative positions of the transactivator gene and a cassette containing tet operator sequences upstream of the p35/p35m minimal promoter and LqhIT are indicated.

Applicant has provided 27 sequence listings in conformity with 37 C.F.R. 1.821–1.825 and Appendices A and B ("Requirements for Application Disclosures Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No. 2 to OJ EPO, 12/1992.

SEQ ID NO:1. BglII linker used in the construction of plasmid TV3tTa.

SEQ ID NO:2. Nucleotide sequence of the 407 bp Xho I to Bam HI restriction fragment from the plasmid pF43h, containing the minimal hGH promoter fused in tandem to seven tetracycline operator sequences.

SEQ ID NO:3. NotI linker used in the construction of plasmid ptetophGH.

SEQ ID NOs:4–13. Synthetic oligonucleotides used to construct the LqhIT2 gene. Oligonucleotide Lq1 encodes the Bombyxin signal peptide. Oligonucleotides Lq1 (SEQ ID NO:4) and Lq10 (SEQ ID NO:13) were used as primers for PCR amplification of the synthetic gene.

SEQ ID NO: 14. Nucleotide sequence of the synthetic DNA fragment encoding the Bombyxin signal peptide followed by the coding region for the LqhIT2 toxin.

SEQ ID NOs:15 and 16. Nucleotide sequences of PCR primers TETR1 and TETR2 used to amplify the tetR portion of tTA.

SEQ ID NO: 17. Nucleotide sequence of the tetracycline repressor gene (tetR) which was amplified by PCR using oligonucleotides TETR1 and TETR2.

SEQ ID NOs:18 and 19. Nucleotide sequences of PCR primers IE1A1 and IE1A2 used to amplify a 454 bp fragment from plasmid pIE1H/C corresponding to the first 145 amino acid residues of IE1.

SEQ ID NO:20. Nucleotide sequence of the activation domain of IE1 (IE1A) which was amplified by PCR using oligonucleotides IE1A1 and IE1A2.

SEQ ID NO:21. Amino acid sequence of tetrIE1A.

SEQ ID NO:22. Nucleotide sequence of the BamHI fragment containing the SV40 polyadenylation signal.

SEQ ID NOs:23 and 24. Nucleotide sequences of two complementary oligonucleotides, P35PRO1 (SEQ ID NO:23) and P35PRO2 (SEQ ID NO:24), that, when annealed, represent the p35 minimal promoter from −8 to −57 bp relative to the translation initiation codon of the p35 gene.

SEQ ID NOs:25 and 26. Nucleotide sequences of two complementary oligonucleotides, P35MPRO1 (SEQ ID NO:25) and P35MPRO2 (SEQ ID NO:26), that, when annealed, represent a modified p35 minimal promoter wherein a single base pair change has been incorporated into the promoter sequence that eliminates the late TTAAG RNA start site.

DETAILS OF THE INVENTION

Disclosed is a method to suppress the expression of insecticidal proteins by recombinant NPVs for in vivo and in vitro production purposes. In one embodiment, a gene encoding a regulatory protein is stably integrated into the genome of an insect or insect cell that is a natural host for insect baculoviruses. In turn, a regulatory sequence that is responsive to the regulatory protein is stably introduced into the genome of a baculovirus at one or more locations near a promoter and/or enhancer element that directs expression of a heterologous protein. Upon introduction into the host (i.e., infection of the transgenic insect or transfection of transgenic insect cells with the recombinant baculovirus), the regulatory protein expressed by the transgenic insect or insect cells will interact with the regulatory sequence present on the baculovirus genome and affect expression of the gene or genes that are controlled by that regulatory sequence. Alternatively, both the gene encoding the regulatory protein operably linked to an inducible, repressible or viral promoter, and the gene encoding the heterologous gene of interest that is operably linked to regulatory sequences that are responsive to the regulatory protein are present in the recombinant NPV genome. These recombinant viruses are then propagated in wild-type insects or insect cells. In the presence of an appropriate inducer or repressor of gene expression of the regulatory protein, control of heterologous gene expression will be affected.

For example, a structural gene encoding the tetracycline (tet) repressor protein that is under the control of a constitutive promoter (e.g., actin promoter) or a viral promoter (preferably a promoter derived from a nuclear polyhedrosis virus) can be inserted into the genome of a lepidopterous insect. Regulatory sequences that are responsive to the tet repressor are introduced into the viral genome proximal to the promoter and/or enhancer regions that control expression of an insecticidal protein. The tet repressor binds to the regulatory sequence(s) and prevents transcription of the gene encoding the insecticidal protein. Lack of expression of this insecticidal protein will delay the onset of paralysis and death of the infected insect, and result in an increase in production of PIBs. In similar fashion, this strategy can be used to control the expression of cytotoxic proteins or proteins that render the virus unstable, thus maximizing virus yields in insect cell culture systems.

In the context of the present disclosure, a number of terms and abbreviations shall be used. "NPV" stands for Nuclear Polyhedrosis Virus, a baculovirus. "Polyhedrosis" refers to any of several virus diseases of insect larvae characterized by dissolution of tissues and accumulation of polyhedral granules in the resultant fluid. "PIBs" are polyhedral inclusion bodies. "AcNPV" stands for the wild-type *Autographa californica* Nuclear Polyhedrosis Virus. "LqhIT2" represents the insect-selective neurotoxin derived from *Leiurus quinquestriatus hebraeus*. "AaIT" represents the insect-selective neurotoxin derived from *Androctonus australis*. "AcLqhIT2" is a short-hand form representing AcNPV that has been genetically modified to harbor the gene encoding LqhIT2 under the transcriptional control of the baculovirus very late p10 promoter.

"Expression" refers to the transcription and translation of a structural gene to yield the encoded protein. As will be appreciated by those skilled in the art, structural gene expression levels are affected by the regulatory sequences (promoter, polyadenylation sites, enhancers, etc.) used and by the host cell in which the structural gene is expressed.

Suitable "regulatory sequences" refer to nucleotide sequences located upstream (5'), within, and/or downstream (3') to a structural gene. The regulatory sequences control the transcription and/or expression of the coding sequences, potentially in conjunction with the protein biosynthetic apparatus of the cell. These regulatory sequences include promoters, operators, enhancer elements, transcription termination sequences, and polyadenylation sequences.

"Regulatory proteins" are proteins that recognize and bind to regulatory sequences and thereby affect transcription and/or expression of the coding sequences. Regulatory proteins may exhibit a negative effect on gene expression (i.e., reduce or eliminate transcription and/or translation) and may therefore be referred to as "repressors". In contrast, certain regulatory proteins may exhibit a positive effect on gene expression (i.e., initiate or increase transcription and/or translation) and may therefore be known as "activators", "transactivators" or "inducers".

"Operator" refers to a regulatory sequence which is recognized by a regulatory protein that modifies the rate of transcription initiation at an adjacent promoter.

"Promoter" refers to the nucleotide sequences, generally found at the 5' end of a structural gene, which direct the initiation of transcription. Promoter sequences are necessary, but not always sufficient, to drive the expression of a downstream gene. Usually promoters drive transcription preferentially in the downstream direction, although promotional activity can be demonstrated (at a reduced level of expression) when the gene is placed upstream of the promoter. Thus, in the construction of heterologous promoter/structural gene combinations, the structural gene is placed under the regulatory control of a promoter such that the expression of the gene is controlled by promoter sequences. The promoter is positioned preferentially upstream to the structural gene and at a distance from the transcription start site that approximates the distance between the promoter and the gene it controls in its natural setting. As is known in the art, some variation in this distance can be tolerated without loss of promoter function.

"Minimal promoter" refers to an RNA polymerase class II promoter generally comprised of a sequence of DNA known as a TATA box that binds RNA polymerase and short stretches of surrounding DNA sequences that, in the absence of additional promoter or operator elements, is unable to support transcription initiation. "Ubiquitous promoter" refers to a promoter which is active (i.e., able to support transcription of its adjacent gene) in all tissues and organs of the organism. "Inducible promoter" refers to a promoter whose function is controlled by the binding or release of particular intracellular trans-acting factors. Inducible promoters are distinguished from constitutive promoters which are unregulated and so are continually active.

The "3' non-coding sequences" refer to the DNA sequence portion of a gene that contains a polyadenylation signal and any other regulatory signal capable of affecting MRNA processing or gene expression. The polyadenylation signal is usually characterized by affecting the addition of polyadenylic acid tracts to the 3' end of the mRNA precursor.

"Gene" refers to the entire DNA portion involved in the synthesis of a protein. A gene embodies the structural or coding portion which begins at the 5' end from the translational start codon (usually nucleotides ATG) and extends to the stop (nucleotides TAG, TGA or TAA) codon at the 3' end. It also contains a promoter region, usually located 5' or upstream to the structural gene, which initiates and regulates the expression of a structural gene. Also included in a gene are the 3' non-coding sequences. "Chimeric" gene refers to an artificial gene comprising heterogeneous regulatory and coding sequences. "Heterologous" gene refers to genes or parts of genes not normally found in the host organism but that have been introduced by gene transfer. "Nucleic acid fragment" refers to nucleotide sequences that are identified with particular functions within a gene.

"Structural gene" is that portion of a gene comprising a DNA segment encoding a protein, polypeptide or a portion thereof and excluding the 5' and 3' sequences involved in regulatory control of gene expression. The structural gene may be one which is normally found in the cell or one which is not normally found in the cellular location wherein it is introduced, in which case it is termed a heterologous gene. A heterologous gene may be derived in whole or in part from any source known to the art, including a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns which are not expressed and which are bounded by the appropriate splice junctions. The structural gene may be a composite of segments derived from a plurality of sources, naturally occurring or synthetic. The structural gene may also include fused genes which encode a fusion protein.

"Synthetic gene" refers to a DNA sequence of a structural gene that is chemically synthesized in its entirety or for the greater part of the coding region. As exemplified herein, oligonucleotide building blocks are synthesized using procedures known to those skilled in the art and are ligated and annealed to form gene segments which are then enzymatically assembled to construct the entire gene. As is recognized by those sllled in the art, functionally and structurally equivalent genes to the synthetic genes described herein may be prepared by site-specific mutagenesis or other related methods used in the art.

The term "operably linked" refers to nucleic acid sequences on a single nucleic acid molecule which are associated so that the function of one is affected by the other. For example, a promoter is operably linked with a structural gene when it is capable of affecting the expression of that structural gene (i.e., that the structural gene is under the transcriptional control of the promoter).

"Transfection" refers to stably introducing a DNA segment carrying a gene into an organism that did not previously contain that gene. "Co-transfection" refers to simultaneous introduction of more than one DNA segment into an organism.

"Transgenic insect" refers to an insect comprised of cells that contain one or more transgenes. "Transgenes" are genes that are introduced into the genome of a cell from which a transgenic organism develops and which remain in the mature organism, thereby directing expression of their encoded products in one or more cell types or tissues of said transgenic organisms.

"Chemically synthesized", as related to a sequence of DNA, means that the component nucleotides were assembled in vitro. Manual chemical synthesis of DNA may be accomplished using well established procedures (19), or automated chemical synthesis can be performed using one of a number of commercially available machines.

It is understood that "an insect cell" refers to one or more insect cells maintained in vitro as well as one or more cells found in an intact, living insect.

"Baculovirus" refers to a group of viruses that only infect arthropods, a phylum that includes the genus Lepidoptera. Insecticidal baculoviruses have great potential to provide an environmentally benign method for agricultural insect pest control. However, improvements to efficacy are required in order to make these agents competitive with current chemical pest control agents. One approach for making such improvements is through genetic alteration of the virus. For instance, it may be possible to modify the viral genome in order to improve the host range of the virus, to increase the environmental stability and persistence of the virus, or to improve the infectivity and transmission of the virus. In addition, improving the rate at which the virus acts to compromise the infected insect would significantly enhance the attractiveness of insecticidal baculoviruses as adjuncts or replacements for chemical pest control agents. One method for increasing the speed with which the virus affects its insect host is to introduce into the baculovirus foreign genes that encode proteins that are toxic to the insect wherein death or incapacitation of the insect is no longer dependent solely on the course of the viral infection, but instead is aided by the accumulation of toxic levels of the foreign protein. The results are insecticidal recombinant baculoviruses.

Many arthropods produce a mixture of insecticidal proteins referred to as venom. These toxic substances are synthesized in specialized glandular tissues, which, when directed by a stinging or piercing apparatus, are capable of paralyzing the arthropod's prey. Small, slow moving or stationary arthropods have adapted a strategy to instantaneously paralyze their prey by utilizing neurotoxic components of the venom at very low concentrations. These components or neurotoxins interfere with the function of insect nervous tissues through efficient competition for certain receptor sites. Many of these neurotoxins are polypeptides. These have been divided into different classes based on their host specificity and mode of action (20). For example, neurotoxic peptides isolated from numerous species of scorpions have been divided into classes that affect arthropods and classes that affect mammals.

Several of the arthropod-specific toxins have been identified as insect-selective peptides. For example, the Buthinae scorpions express two types of insect-selective neurotoxins that differ in their biological effects on target insects. In the blowfly, those classified as excitatory toxins cause immediate, fast and reversible contractive paralysis due to induction of repetitive firing of the terminal branches of the motor neurons (21–23). These toxins are single-chained polypeptides of approximately 70 amino acids and are cross-linked by four disulfide bridges. The excitatory effect is attributed to an increase in the activatable action potential, sodium conductance, and a voltage-dependent slowing of the channel's closure. AaIT, a toxin produced from the venom of the scorpion *Androctonus australis* (24), was the first insect toxin isolated from these organisms that exhibited this excitatory action.

A second class of insect-selective neurotoxins are the depressant toxins, including BjIT2 (25), LqqIT2 (26) and LqhIT2 (27). These toxins are polypeptides of 60 to 65 amino acids which possess primary amino acid sequences that are distinct from the excitatory toxins. These toxins induce a slow, progressive paralysis and complete relaxation of the musculature of the insect. This activity is the result of the blockage of evoked action potentials (26, 28), and is attributable to the suppression of the activatable sodium conductance and depolarization of the axonal membrane.

The methods and strategies used for preparation of recombinant baculovirusea that express heterologous genes are well known in the art (4, 5, 29). These methods of gene expression provide economical preparation of mammalian proteins in a eukaryotic expression vector system, in many instances yielding proteins that have achieved their proper tertiary conformation and formed the proper disulfide bridges necessary for activity.

Commonly, the introduction of heterologous genes into the baculovirus genome occurs by homologous recombination between viral genomic DNA and a suitable "transfer vector" containing the heterologous gene of interest. These transfer vectors are generally plasmid DNAs that are capable of autonomous replication in bacterial hosts, affording facile genetic manipulation. Baculovirus transfer vectors also contain a genetic cassette comprising a region of the viral genome that has been modified to include the following features (fisted in the 5' to 3' direction): 1) viral DNA comprising the 5' reigon of a non-essential genomic region; 2) a viral promoter; 3) one or more DNA sequences encoding restriction enzyme sites facilitating insertion of heterologous DNA sequences; 4) a transcriptional termination sequence; and 5) viral DNA comprising the 3' region of a non-essential genomic region. A heterologous gene of interest is inserted into the transfer vector at the restriction site downstream of the viral promoter. The resulting cassette comprises a chimeric gene wherein the heterologous gene is under the transcriptional control of the viral promoter and transcription termination sequences present on the transfer vector. Moreover, this chimeric gene is flanked by viral DNIA sequences that facilitate homologous recombination at a non-essential region of the, viral genome. Recombinant viruses are created by co-transfecting insect cells that are capable of supporting viral replication with viral genomic DNA and the recombinant transfer vector. Homologous recombination between the flanking viral DNA sequences present on the transfer vector and the homologous sequences on the viral genomic DNA takes place and results in insertion of the chimeric gene into a region of the viral genome that does not disrupt an essential viral function. The infectious recombinant virion consists of the recombined genomic DNA, referred to as the baculovirus expression vector, surrounded by a protein coat.

In a preferred embodiment, the non-essential region of the viral genome that is present on the transfer vector comprises the region of the viral DNA responsible for polyhedrin production. Most preferred is a transfer vector that contains the entire polyhedrin gene between the flanking sequences that are involved in homologous recombination. Recombination with genomic DNA from viruses that are defective in polyhedrin production (due to a defect in the genomic copy of the polyhedrin gene) will result in restoration of the polyhedrin-positive phenotype. This strategy facilitates identification and selection of recombinant viruses.

In another embodiment, baculoviral genomic DNA can be directly modified by introduction of a unique restriction enzyme recognition sequence into a non-essential region of the viral genome. A chimeric gene comprising the heterologous gene to be expressed by the recombinant virus and operably linked to regulatory sequences capable of directing gene expression in baculovirus-infected insect cells, can be constructed and inserted directly into the viral genome at the unique restriction site. This strategy eliminates both the need for construction of transfer vectors and reliance on homologous recombination for generation of recombinant viruses. This technology is described by Ernst et al. (30), and in WO94/28114 (31).

Recombinant baculovirus expression vectors suitable for delivering genetically encoded insect-specific neurotoxns require optimal toxin gene expression for maximum efficacy. A number of strategies can be used by the skilled artisan to design and prepare recombinant baculoviruses wherein toxin gene expression results in sufficient quantities of toxin produced at appropriate times during infection in a functional form and assailable for binding to target cells within the insect host.

One key to optimal mass production of recombinant NPVs is selection of an appropriate system to regulate gene expression. Such a system preferably uses a repressor/operator element that suppresses transcription of the gene encoding the insecticidal activity. Several repressor systems have been described that affect gene expression, including various inducible eukaryotic promoters (32–33).

In addition, regulation of gene expression in eukaryotic cells can be achieved through the use of the lac repressor/operator inducer system of *Escherichia coli*. Three approaches have been described: (i) prevention of transcription initiation by propiely placed lac operators at promoter sites (34–38); (ii) blockage of transcription mediated by RNA polymerase II during elongation by a lac repressor/operator complex (39); and (iii) activation of a promoter responsive to a fusion protein comprised of the lac repressor protein and the activating domain of virion protein 16 (VP16) of herpes simplex virus (40–41). However, due to slow and inefficient activation by the lac inducer isopropyl-β-D-thiogalactopyranoside (IPTG), this system has resulted in only moderate regulation (42).

The present invention specifically concerns the construction of a system for regulatable gene expression employing the tetracycline (tet) operator-repressor systenm. The tetracycline repressor is a DNA-binding protein with high affinity for the tet operator sequence. The Tn10-encoded tet repressor regulates the expression of genes by binding to operator site(s) which overlap a promoter(s) (43,44). Tetracycline or an analog of tetracycline prevents the repressor from binding to its operator sequence, thus allowing RNA polymerase to bind to the promoter sequences and mediate mRNA transcription.

The tet operator-repressor system has been used successfully in plants to effectively control gene expression. For instance, Gatz et al. were able to use this system to reduce the activity of a constitutive promoter (cauliflower mosaic virus 35S proroter; CaMV 35S) by 500 fold in transgenic plants (45). Specifically, they generated a transgenic tobacco plant that synthesized $1\times10^6$ tet repressor molecules per cell. Three tet operators were introduced into the vicinity of the TATA box of the CaMV 35S promoter. Under normal physiological conditions gene expression was essentially inhibited. However, addition of tetracycline prevented the repressor from binding to the operator sites, causing full derepression of the CaMV 35S promoter.

More recently, the tet operator-repressor system has been used to control gene expression in the protozoan parasite *Trypanosoma brucei* (46). Transgenic trypanosomes expressing the tetracycline repressor of *E. coli* exhibited inducer (tetracycline)-dependent expression of chromosomally integrated reporter genes under the control of a promoter bearing a tet operator. Reporter expression could be controlled over a range of four orders of magnitude in response to tetracycline concentration; this far exceeds transcriptional regulation exhibited by other eukaryotic repression-based systems.

The instant invention controls expression of an insecticidal protein encoded by a recombinant virus genome. Experimental evidence demonstrates a greater than approximately 10-fold decrease in yield of PIBs from insects infected with recombinant NPVs genetically engineered to express an insecticidal protein relative to PIB yield from insects treated with wild-type viruses (see FIG. 1). Certain insecticidal proteins can have adverse effects on insect cells (e.g., cytotoxicity) or can induce paralysis and death of an insect host. These effects can result in a reduction in viral progeny and/or an unstable viral construct. Suppressing the expression of the insecticidal protein would give the insect host cell the ability to support propagation of recombinant viruses to yields that approach yields of wild-type viruses.

This invention regulates toxin gene expression by several methods. One method uses a tetracycline-controlled transactivator molecule (also referred to herein as "tetracycline transactivator protein") to control the promoter directing expression of the toxin gene. Aspects of this tightly regulatable expression system are described in U.S. Pat. No. 5,464,758, incorporated herein by reference, and by Gossen & Bujard (47, 48), and are depicted in FIG. 2. The control element used for gene regulation is a fusion protein comprised of the tet repressor protein filsed to the activating domain of virion protein 16 of herpes simplex virus (tTA).

The invention also includes construction of a transgenic insect that constitutively expresses a repressor (or repressor-like) protein. When a recombinant NPV containing a chimeric gene (comprised of an operably linked tet operator(s), promoter and toxin structural gene) is replicating in the transgenic host, the repressor binds to the operator(s) and inhibits expression of the toxin. To construct this conditional regulatory system for gene transcription, two basic genetic manipulations are performed: i) tet operator(s) fragments are inserted upstream of the toxin gene, preferably at a region which overlaps with the transcription initiation site and/or enhancer region; and ii) the repressor gene is stably engineered into the genome of a eukaryotic cell, preferably an insect or insect cell line.

The repressor may be placed under the control of a constitutive promoter (i.e., actin) or baculovirus promoter (i.e., IE1, p10 or hybrid promoter) in order to drive expression of the repressor during infection of the host by recombinant virus. Using a baculovirus promoter such as IE1, p10, or polyhedrin, the repressor is expressed only at the time of viral infection. This design provides for adequate expression of the repressor protein, since the virus provides the transcriptional machinery needed for viral replication. The tet operator site(s) is placed into the viral genome proximal to the transcription start site and/or enhancer regions in order to block transcription of the heterologous protein (preferably an insecticidal protein) driven by the viral promoter.

High efficiency vectors for insertion of foreign genes into the insect genorie are required for this strategy. Mobile nucleic acid entities of various types have been identified in different insects (49). Insertion of mobile elements into DNA sequences car result in altered or disrupted gene expression which can be identified as mutant phenotypes. Currently, high efficiency transformation of insects is achieved using the P-element based transformation vector system in Drosophila (50). However, these transformation vectors cannot be used for transformation of other insects (51). Therefore, alternative mobile genetic elements which have utility in other insects, including the high-efficiency transformation of lepidopterous insects, are required.

In addition, other transformation methods have focused on alternative delivery systems. One such technique is "maternal microinjection" which involves the injection DNA into eggs or ovaries within the gravid female. This technique has been successfully used to introduce plasmid DNA sequences into the predatory mites *Metaseiulus occidenialis* (52) and *Amblyseius finlandicus* (53). Recently, electroporation has also been reported to successfully deliver plasmid DNA to insect embryos (Keith Hughes, USDA, Fargo, N.Dak., personal communication).

One method to prepare a transgenic insect is to use a transposable-like element (TE) useful for introducing heterologous genes into the genome of lepidopteran insects. These genetic elements facilitate construction of transgenic insects capable of expressing regulatory proteins that, in turn, control baculovirus gene expression. One such TE is the mariner element which is widespread in arthropod genomes, and nearly ubiquitous in lepidopterous insects (55). The mariner element can be identified and prepared using degenerate primers derived from two conserved regions of the mariner transposase open reading frame. Recently, a mariner transposable element was isolated from the predatory mite, *Metaseiulus occidentalis* (55). Using two inverse primers, the complete mariner element (Moc1) was sequenced and found to be 1284 bp in length, including 28 bp inverted terminal repeat sequences. However, the Moc1 mariner element contains numerous mutations, including frame shifs, and transposase activity can not be detected. Based on these observations Moc1 is considered to be an inactive transposable element. However, an inactive mariner element is an attractive tool for introduction of exogenous DNA by homologous recombination, because it has accumulated numerous mutations, including deletions, insertions and stop codons. Insertion of exogenous DNA into such a mariner locus should be advantageous since the transposase gene is no longer viable and such exogenous DNA will remain stable. The insertion of the tet repressor gene and a selectable marker (e.g., cyclodiene resistance gene—Rd1; (56, 57) containing a mariner fragment into a mariner locus in a lepidopterous insect occurs by homologous recombination. Transformation is carried out by previously described microinjection techniques or newly developed electroporation protocols.

EXAMPLES

The present invention is firher defined in the following examples. It will be understood that the examples are given for illustration only and the present invention is not limited to use described in the examples. From the above discussion and the following examples, one skilled in the art can ascertain, and without departing from the spirit and scope thereof, can make various changes and modifications of the invention to adapt it to various usages and conditions. All such modifications are intended to fall within the scope of the intended claims.

Example 1

Regulating expression of an insecticidal protein can also be achieved by incorporating the tTA and operator sites into the viral genome itself In this method, tht control elements of the tetracycline resistance operon encoded in Tn10 of *E. coli* were inserted into the AcNPV genome in order to regulate the expression of insecticidal protein(s). The tTA was placed under the control of the immediate early promoter IE1 which expresses foreign genes immediately following infection by NPV. The baculovirus transfer vector pAcP+IE1TV3 (provided by Dr. Donald Jarvis, Texas Agricultural Experiment Station, Texas A&M University, College Station, Tex.) was used for this construction and is a derivative of the baculovirus early promoter transfer vectors described in U.S. Pat. No. 5,162,222. Initially, the tTA was excised from the plasmid pUHD15-1 (obtained from Dr. Robert Horlick, DuPont-Merck Pharmaceutical Co., Wilmington, Del.) by the enzymes EcoRI and BamHI and inserted into the plasmid Bluescript SK±® (Stratagene, Menasha, Wis.) digested with EcoRI and BamHI. Following ligation, plasmid DNA was transformed into *E. coli* DH5α (Gibco/BRL; Gaithersburg, Md.), and presence of the insert was confirmed by restriction enzyme analysis.

Following confirmation of the tTA inert, an SV40 polyadenylation fragment (SEQ ID NO:22) (provided by Gary Chun, E. I. du Pont de Nemours and Company) with BamHI restriction sites at the 5' and 3'-ends was inserted at the BamHI restriction site in Bluescript SK±® directly downstream of the tTA The insert was confirmed for correct orientation using an internal HpaI site (poly A) and an XhoI site found in the 3' end of the multiple cloning site of Bluescript SK±®. The new plasmid containing the tTA and poly A fragment was digested with EcoR1 and filled in with Klenow Polymerase, and a BglII restriction site was added by incorporation of a BglII linker (SEQ ID NO:1). Following ligation, plasmid DNA was transformed into the *E. coli* DH5α. The fragment containing the tTA and SV40 was then excised from this modified Bluescript SK±® plasmid with the restriction enzymes BglII and NotI. This fragment was ligated into the transfer vector pAcP+IE1TV3 cut with BglII and NotI. This construct resulted in the insertion of the synthetic structural gene encoding tTA and polyadenylation fragment downstream of the baculovirus IE1 promoter and the hr5 enhancer region. Following ligation, plasmid DNA was transformed into the *E. coli* DH5α and resultant transformants were screened for possession of plasmids that contained a unique asymmetric site located at the 3' end of the tTA gene. The new plasmid was labeled TV3tTa (FIG. 3).

The next step to construct a regulatory system for a recombinant baculovirus insecticide involved incorporating a minimal promoter sequence and tetracycline operator sequences into the viral genome. The restriction enzymes XhoI and BamHI were used to excise a minimal promoter (hGH) fused to tandem tetracycline operator sequences (7 tet operators) from the plasmid pF43h (SEQ ID NO:2; obtained from Dr. R. Horlick, DuPont-Merck Pharmaceutical Co.). This fragment was cloned into Bluescript SK±® that was previously digested with XhoI and BamHI. Following ligation, plasmid DNA was transformed into the *E. coli* DH5α and positive clones were identified by restriction enzyme analysis. This plasmid was then digested with the restriction enzyme XhoI (at 3' end of multiple cloning site), filled in with Klenow Polymerase and relegated in the presence of a NotI linker (SEQ ID NO:3). Following ligation, plasmid DNA was transformed into *E. coli* DH5α and resultant transformants were screened by digestion with the restriction enzyme NotI. The presence of an approximately 450 bp fragment following electrophoresis through a 2% agarose gel confirms the existence of the proper construct. This plasmid is known as ptetophGH.

Finally, a structural gene encoding an insect-selective neurotoxin, LqhIT2, is placed downstream of the minimal promoter into the BamHI cloning site. In order to prepare the LqhIT2 gene, ten oligonucleotides were designed (FIG. 4; composite of SEQ ID NO:4–13) and synthesized by standard phosphoramadite chemistry. These oligonucleotides were phosphorylated using Gibco/BRL (Gaithersburg, Md.) kinase, annealed, and ligated using Gibco/BRL ligase following the scheme depicted in FIG. 5, and employing the manufacturer's recommended protocols. Ligated fragments were then amplified by employing the polymerase chain reaction (PCR) using Perkin-Elmer Cetus AmpliTaq® Polymerase (Norwalk, Conn.) according to the manufacturer's protocol and the modifications described below. Oligonucleotide Lq1 (SEQ ID NO:4) was used as the forward primer and oligonucleotide Lq10 (SEQ ID NO:13) served as the reverse primer. The descriptions of these protocols are set out below in greater detail.

Ten separate phosphorylation reactions (one for each oligonucleotide) were carried out. Two-hundred and fifty pmol of each oligonucleotide (SEQ ID NO:4–13) were placed in a 1.5 mL microcentrifuge tube. Five uL of 10×kinase buffer, 1 uL of 1 mM ATP, 6 uL of kinase (Gibco/BRL, 10 units/uL), and a sufficient volume of water was added to each tube in order to bring the total reaction volume to 50 uL. The ten tubes were incubated at 37° C. for 1 h. Following incubation, 5 uL of each phosphorylated oligonucleotide (25 pmol) was placed into a single microcentrifuge tube, and the tube was placed into a dry heat blockset at 95° C. The heat block was then turned off and allowed to cool to room temperature to facilitate annealing of phosphorylated oligonucleotides. Fifty uL of the mixture of phosphorylated, annealed oligonucleotides were placed into a separate microcentrifuge tube along with 15 uL of 5×ligase buffer, 3 uL of 10 mM ATP, 4 uL of ligase enzyme (Gibco/BRL, 5 units/uL) and 3 uL of deionized water. This tube was incubated at 37° C. for 30 min and subsequently stored at room temperature overnight.

The synthetic nucleic acid fragment comprising the annealed and ligated oligonucleotides was amplified by PCR. Three PCR reactions were performed on varying dilutions of template DNA (comprising the phosphorylated, annealed and ligated oligonucleotides). The following reaction mix was employed for PCR reactions:

61.5 uL of deionized water
10 uL of 10×PCR buffer (Perkin-Elmer Cetus)
2 uL each of dATP, dCTP, dGTP, dTTP (200 uM each)
0.5 uL of AmpliTaq® Polymerase (2.5 units/100 uL)
Template DNA was diluted 1:100, 1:1,000 and 1:10,000 (v/v) with deionized water. Eighty uL of the reaction mix was placed in each of three 0.5 mL microcentrifuge tubes. Five uL (100 pmol) of oligonucleotide Lq1 (SEQ ID NO:4) and 5 uL (100 pmol) of oligonucleotide Lq10 (SEQ ID NO:13), (serving as the forward and reverse PCR primers, respectively), was added to each tube. Ten uL of appropriately diluted template was added to each tube. PCR reactions were carried out using a Perkin-Elmer DNA Thermocycler® programmed to carry out the following amplification protocol:

| STEP 1 (1 cycle): | 96° C. | 3 minutes |
|---|---|---|
| | 75° C. | 3 minutes |
| STEP 2 (25 cycles): | 95° C. | 30 seconds |
| | 75° C. | 2 minutes |
| STEP 3 (1 cycle): | 95° C. | 30 seconds |
| | 75° C. | 5 minutes |

Products resulting from amplification were analyzed by electorphoresis through a 2% agarose gel. An amplified fragment of approximately 300 base pairs was observed for each reaction.

Following PCR amplification of the LqhIT2 gene and flanking regions, the 300 bp band was isolated from a 2.0% agarose gel and purified using a SpinBind® DNA recovery system (FMC, Rockland, Me.) according to the manufacturer's protocol. The isolated fragment was digested with BamHI in order to create cohesive 5' and 3' ends of the synthetic oligonucleotide containing the LqhIT2 gene and signal sequence (FIG. 6; SEQ ID NO:14). The digested fragment was then inserted into the pTZ-18R plasmid (Pharmacia, Piscataway, N.J.) at the BamHI cloning site using standard molecular cloning techniques. Following transformation of *E. coli* DH5αMCR, isolated colonies were chosen and plasmid DNA was prepared. Eight positive clones were identified and sequenced with the commercially available forward and reverse primers of pTZ-18R One clone (No. 16) was found to contain the correct sequence encoding for synthetic gene and signal sequence. The resulting plasmid (pTZ-18RLq) contained two BamHI restriction sites: one site near the 5' end of the toxin gene and the other site following the stop codon.

pTZ-18RLq plasmid DNA was prepared according to standard protocols, and was digested with BamHI to release the inserted 300 base pair fragment containing the LqhIT2 gene and signal sequence. This fragment was separated from vector sequences by electrophoresis through a 1.2% agarose gel, and purified using a SpinBind® DNA recovery system. The isolated fragment was then inserted into the BamHI cloning site of ptetophGH using standard molecular cloning techniques. Following transformation into *E. coi* DH5αMCR, isolated colonies were chosen and plasmid DNA was prepared.

This plasmid was then digested with the restriction enzyme NotI, liberating a 750 bp fragment that was isolated from a 2.0% agarose gel and purified using a SpinBind® DNA recovery system. This fragment contains the tet operator sites, minimal hGH promoter and LqhIT2 gene/leader sequence. The isolated and digested fragment was then inserted into the new baculovirus transfer vector, TV3tTa (supra), at the NotI cloning site, using standard molecular cloning techniques. Following transformation into *E. coli* DH5αMCR, isolated colonies were chosen and plasmid DNA was analyzed by restriction enzyme analysis. Several colonies containing the NotI fragment were isolated, propagated, and plasmid DNA was prepared for cotransfection. The new transfer vector is labeled TV3tTaTo-LqhIT2 (see FIG. 7).

*Spodoptera frugiperda* cells (Sf-9) were propagated in ExCell® 401 media (JRH Biosciences, Lenexa, Kans.)

supplemented with 3.0% fetal bovine serum. Lipofectin® (50 μL at 0.1 mg/mL, Gibco/BRL) was added to a 50 μL aliquot of TV3tTaTo-LqhIT2 (500 ng) and linearized polyhedrin-negative AcNPV (2.5 μg, Baculogold® viral DNA, Pharmigen, San Diego, Calif.). Sf-9 cells (approximate 50% monolayer) were co-transfected with the viral DNA/transfer vector solution. The supernatant fluid from the co-transfection experiment was collected at 5 days post-transfection and recombinant viruses were isolated employing standard plaque purification protocols, wherein only polyhedrin-positive plaques are selected (6).

Isolated plaques were picked and suspended in 500 μL of ExCell® media supplemented with 2.5% fetal bovine serum. Sf-9 cells in 35 mM petri dishes (50% monolayer) were inoculated with 100 μL of the viral suspension, and supernatant fluids were collected at 5 days post infection. These supernatant fluids were used to inoculate cultures for large scale propagation of recombinant viruses.

Expression of LqhIT2 encoded by the recombinant baculovirus AcTV3tTaTo-LqhIT2 is confinned by immunoblot analysis and bioassay. Sf-9 cells (50 mL) are infected with wild-type AcNPV (negative control), AcLqhIT2 (positive control), or AcTV3tTaTo-LqhIT2. In the absence of tetracycline or an analog, heterologous protein is expressed efficiently in AcTV3tTaTo-LqhIT2-infected cells. However, in the presence of tetracycline or an analog, the expression of the toxin is suppressed. Subsequent additional studies are conducted using different concentrations of tetracycline added to the media in order to determine the ability of the substrate to effectively control the expression of the heterologous protein. At several intervals post infection, infected cells are collected and growth media is removed by centrifugation of cell suspensions. Spent culture media is decanted and the remaining cells are lysed with a Branson Sonifier® (Model 450) for 30 sec at setting 2. Cellular debris is then removed by centrifugation at 15,000 rpm for 10 min in a refrigerated microcentrifuge (4° C.).

Protein concentrations of infected cell sonicates are quantified using the BCA Protein Assay (Pierce, Rockford, Ill.) according to the manufacturer's instructions. A standard curve is prepared based on known concentrations of Bovine Serum Albumin. Samples and standards are incubated for 30 min at 37° C., and the absorbence at 562 is measured with a spectrophotometer. Protein concentrations are determined for each sample by linear regression analysis.

Individual proteins in quantified samples are separated by protein electrophoresis. Samples are diluted to 3–4 mg/mL protein with deionized water. Twenty-five μL of each sample are added to 75 μL of electrophoresis sample buffer (3.8 mL deionized $H_2O$, 1.0 mL 0.5 M Tris-HCl, pH 6.8, 0.8 mL glycerol, 1.6 mL 10% (w/v) SDS, 0.4 mL β-mercaptoethanol, 0.4 mL 0.5% bromophenol blue). Molecular weight standards are prepared by diluting 1 μL of biotinylated protein molecular weight standards (Gibco) in 100 μL of sample buffer. Samples and standards are heated at 95° C. for 2 min. Samples are loaded (20 μL/well) onto a 15% Mini-Protean II Tris-HCl Ready Gel® (Bio-Rad, Melville, N.Y.). Electrophoresis running buffer (3 g Tris base, 14.4 g glycine, 1.0 g SDS in 1 L deionized $H_2O$) is added to the assembled electrophoresis gel apparatus and samples are electrophoresised for approximately 1.5 h at 40 mA.

Following electrophoresis, separated proteins are transferred from the electrophoretic gel to a nitrocellulose filter by western blotting. Blotter paper (3MM; Schleicher and Schuell, Keene, NH) and nitrocellulose (BA-S NC; Schleicher and Schuell) are cut to the approximate dimensions of the gel and soaked in western transfer buffer (11.6 g Tris base, pH 8.3, 5.8 g glycine, 0.74 g SDS, 400 ML methanol, 1.6 L deionized $H_2O$). The blotter paper, nitrocellulose and gel are assembled in the following sequence: 3 sheets of blotter paper, gel, nitrocellulose, and 3 pieces of blotter paper. This "sandwich" is placed in the transfer apparatus such that the gel is oriented towards the cathode and the nitrocellulose membrane towards the anode. Proteins are transferred by applying a current to the transfer apparatus for 4 h at 60 mA. Following transfer, the apparatus is disassembled and the nitrocellulose filter allowed to air dry.

Immunoblot analysis of transferred proteins proceeds by the following steps, all of which are performed on rotary shaker at room temperature. Sites on the nitrocellulose membrane that are unoccupied by transferred proteins are blocked with 3% (w/v) gelatin dissolved in TTBS (20 mM Tris, 500 mM NaCl, pH 7.5, 0.05% Tween-20) by incubation for 30 min. The blocking solution is removed and the membrane is rinsed in 100 mL TTBS for 5 min. LqhIT2-specific rabbit polyclonal antibody (obtained from Dr. Bruce Hammock, University of California, Davis, Calif.) is prepared by adding 10 μL rabbit antibody to 10 mL TTBS. This primary antibody solution is applied to the blocked nitrocellulose filter and incubated for 1 h. Following this incubation, the nitrocellulose filter is washed in 3 changes of 100 mL TTBS, each wash lasting 10 min. The secondary antibody is prepared by adding 10 μL peroxidase conjugated goat anti-rabbit IgG (Sigma, St. Louis, Mo.) and 10 μL peroxidase-labeled streptavidin to 20 mL TTBS. The nitrocellulose filter is incubated with this solution for 1 h. Following this incubation, the filter is washed in 3 changes of 100 mL TTBS, each wash lasting 10 min. Detection reagent (ECL Detection kit; Amersham, Arling Heights, Ill.) is applied to the nitrocellulose and incubated for 60 sec. The detection reagent is drained from the filter, and the filter covered with Saran Wrap. Signal from the nitrocellulose filter is detected by exposing the processed membrane to X-ray film (Kodak X-OMAT AR, Rochester, N.Y.) for 2–10 sec. Isolates that provide a positive immunoblot response near 7,000 Mr are considered positive for toxin gene.

The conditions described above for carrying out the immunoblot procedure were developed using native LqhIT2 toxin wherein the limit of detection was determined to be 15 ng toxin. In experiments using infected cell sonicates, LqhIT2 toxin encoded by the recombinant baculovirus AcTV3tTaTo-LqhIT2 was not detected, suggesting that the amount of toxin expressed in infected cells and present in the tested samples was below the detection limit of the assay.

Example 2

A new transactivator gene hybrid was constructed which contained the tetR gene fused in frame with the activation domain of the AcMNPV IE-1 gene. The tetR gene portion of tTA was PCR amplified using the following oligonucleotide primers:

TETR1 5'-ATGTCTAGATTAGATAAAAG-3' (SEQ ID NO:15)

TETR2 5'-AGATCTGGACCCACTTTACATTTAAG-3' (SEQ ID NO:16)

The DNA template for this reaction was the plasmid TV3tTa. The following reaction mix was employed for this PCR reaction:

33 uL of sterile deionized $H_2O$ 10 uL of 5×Taq buffer D (InVitrogen)

5 uL of 10×DNTP stock (2.5 mM of each DINTP)

1 uL of oligonucleotide TETR1 (SEQ ID:15)(100 pmol)

1 uL of oligonucleotide TETR2 (SEQ ID:16)(100 pmol)
1 uL of plasmid DNA TV3tTa (10 ng)
0.2 uL of AmpliTaq Polymerase (5 units/uL)
PCR reactions were carried out according to the following amplification protocol:

| STEP 1 (1 cycle): | 95° C. | 1 min |
|---|---|---|
|  | 72° C. | 4 min |
| STEP 2 (30 cycles): | 95° C. | 30 sec |
|  | 45° C. | 30 sec |
|  | 72° C. | 30 sec |
| STEP 3 (1 cycle): | 95° C. | 30 sec |
|  | 45° C. | 30 sec |
|  | 75° C. | 5 min |

The resulting 622 base pair product (SEQ ID NO:17) contains the tetR gene from +1 relative to the translational start codon (ATG) to +616 base pairs of tTA. An extra BglIIH restriction site was incorporated at the 5' end of the oligonucleotide TETR2 for future insertion of the IE-1 activation domain into this site.

Two oligonucleotide primers,
IE1A1
    5'-CGGGATCCATGACGCAAATTAATTTTAACG-3' (SEQ ID:18); and
IE1A2
    5'-CCAGATCTTTAACCTTGTGAATTGTCCAAG TATTC-3' (SEQ ID:19),
were used to amplify a 454 base pair fragment (SEQ ID NO:20) from plasmid pIE1H/C (58) corresponding to the first 145 amino acid residues of IE-1 (IE1A). This region has been reported to represent the activation domain of IE-1 (59). A BamHI or a BglII site (incorporated at the 5' end of IE1A1 and IE1A2, respectively) was added onto the ends of IE1A during amplification to facilitate an inframe insertion of IE1A with tetR (see below). Conditions for PCR amplification of the IE-1 activation domain were identical to those described above for the tetR gene.

Both PCR amplification products, tetR and IE1A, were cloned directly into the plasmid vector PCRII (Invitrogen, San Diego, Calif.) using the TA cloning kit (Invitrogen) resulting in plasmids ptetR and pIE1A, respectively. Several potential clones of ptetR were digested with BamHI and BglII to identity those clones in which tetR was flanked upstream by BamHI and downstream by BglII. The fidelity of both tetR and IE1A were confirmed by sequence analysis. The final hybrid transactivator gene was constructed by digesting pIE1A with BamHI and BglII and inserting the 454 bp fragment containing IE1A into ptetR linearized by partial digestion with BglII. Correct clones in which IE1A was inserted in the same orientation as tetR were identified based on digestions using BamHI and BglII. Only those clones containing tetR inserted inframe with IE1A generated a 1080 base pair fragment. The resulting plasmid, ptetRIE1A, contains a hybrid gene consisting of the tetR gene fused in frame with IE1A (SEQ ID NO:21; FIG. 8). The junction between tetR and IE1A was confirmed by sequence analysis. Also, a BamHI fragment containing the SV40 polyadenylation sequence (SEQ ID NO:22) was cloned immediately downstream of the tetRIE1A gene at the BglII site.

In addition to switching the VP 16 activation domain with the analogous domain from IE1, another modification to the system included the substitution of the human growth hormone (hGH) minimal promoter by the AcMNPV p35 minimal promoter. This promoter contains both early and late transcriptional elements but is predominantly an early promoter (60). Two complementary oligonucleotides (200 pmol), P35PRO1 (SEQ ID NO:23) and P35PRO2 (SEQ ID NO:24) were annealed in 10×ligase buffer (New England Biolabs Inc.) by heating to 100° C. for 5 min and gradually cooling to room temperature over a 1 h period. The resulting annealed products represent the p35 minimal promoter from −8 to −57 bp relative to the translation initiation codon of the p35 gene (FIG. 9). The oligonucleotides were designed such that after annealing to each other, the ends were compatible with SstI; however, only the 3' end of the promoter actually regenerated a SstI site after cloning into an SstI site. The p35 minimal promoter was cloned into the SstI site of the plasmid ptetophGH resulting in the substitution of the p35 promoter for the hGH promoter, and placing the p35 minimal promoter under transcriptional regulation of the tetop sequences. The correct orientation of the p35 promoter relative to the tetop sequences was confirmed by digestion with SstI and sequence analysis. The resulting plasmid was named ptetopp35.

Similarly, a modified p35 minimal promoter was constructed by annealing together, under identical conditions as above, another set of oligonucleotides, P35MPRO1 (SEQ ID NO:25) and P35MPRO2 (SEQ ID NO:26), to generate a p35 promoter in which a single base pair change has been incorporated into the promoter sequence which eliminates the late TTAAG RNA start site (FIG. 10). Removal of the late start site should bring expression of LqhIT2 or other heterologous genes under total transcriptional control of tetRIE1A and reduce the leakiness of the system that may result from transcription from the late start site at late times during infection. The modified p35 minimal promoter was cloned into the SstI site of ptetophGH resulting in plasmid ptetopp35m. Both ptetopp35 and ptetopp35m contain unique BamHI and NotI sites for insertion of DNA downstream of the p35/p35m minimal promoters.

Figure 11:
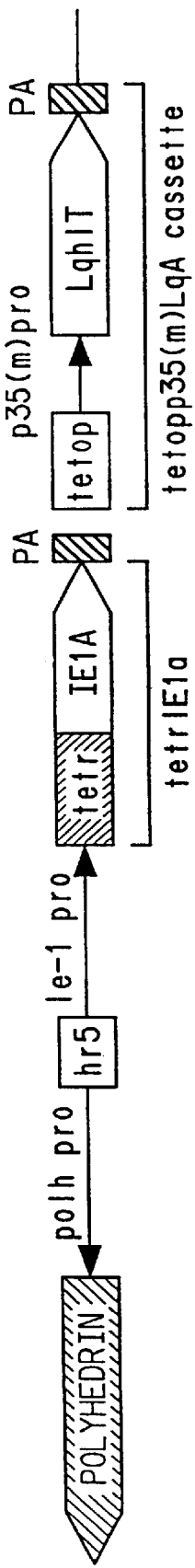

The LqhIT2 gene and leader sequence was isolated from pTV3tTaTo-LqhIT2 by digestion with BamHI and a 300 base pair fragment containing the LqhIT2 gene and leader sequence were subcloned into a unique BglII site in both ptetopp35 and ptetopp35m. The resulting plasmids, ptetopp35Lq and ptetopp35mLq, now contain the LqhIT2 gene/leader sequence immediately downstream of the p35/p35m promoter. Clones containing LqhIT2 in the correct orientation relative to the p35/p35m promoter were identified by digestion with SstI. The tetopp35/p35mLq cassette was completed by inserting a 204 base pair BamHI fragment containing the SV40 polyadenylation signal sequence (SEQ ID NO:22). An internal HpaI site was used to identify clones with the polyA signal sequence in the correct orientation relative to LqhIT2. The final plasmid, ptetopp35/p35mLqA, was used to supply the tetop cassette for insertion into the final transfer vector.

Transfer vectors designed to incorporate tetRIE1A and ptetopp35/p35mLqA into the AcMNPV genome were constructed in two stages. First, the transfer vector pAcP+IE1TV3 (provided by Dr. Donald Jarvis, Texas A & M University, College Station, Tex.) was digested with BglII and NotI (in the multiple cloning site) to linearize the vector. A 1.3 kilobase-pair BamHI/NotI fragment derived from ptetRIE1A was directionally cloned into these sites in pAcP+IE1TV3 placing the transactivator gene under transcriptional control of the hr5/ie-1 promoter. Second, the tetopp35LqA or the tetopp35mLqA cassette was inserted into an unique NotI site regenerated during insertion of tetRIE1A into pAcP+IE1TV3. This was accomplished by digesting the vector with NotI and using the large fragment of DNA polymerase I (Klenow) to fill in the 5' overhanging termini to generate blunt ends. Similarly, ptetopp35/p35mLqA was digested with XhoI and SstII and a 0.8 kbp fragment containing the tetopp35/p35mLqA cassette was blunt-ended using T4 DNA polymerase. This fragment was then inserted into the blunt-ended NotI site. Clones containing each cassette in both orientations relative to the tetRIE1A gene were chosen to generate recombinant virus to determine the effect of orientation on toxin gene expression. These clones were designated either Lq+ or Lq− depending on whether the toxin gene was in the samne or opposite orientation as the transactivator, respectively (FIG. 11). Consequently, four different transfer plasmids (pTV3lq+, pTV3lq−, pTV3Mlq+ and pTV3Mlq−) were constructed.

Figure 12:
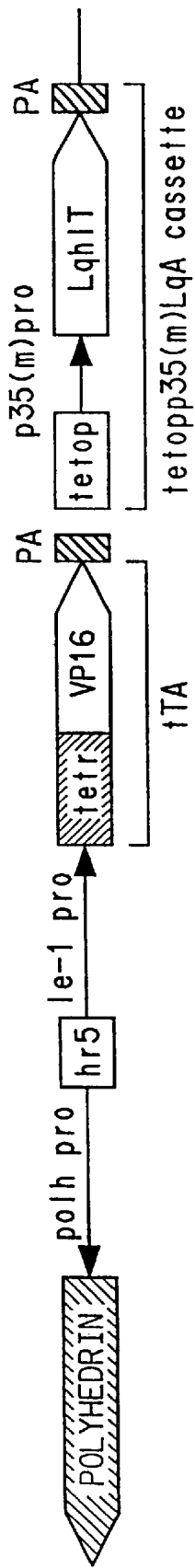

In addition, transfer plasmids were also constructed in which the tetopp35/p35mLqA cassette replaced the tetop-hGH-Lq cassette in pTV3tTaTo-LqhIT2 such that the former cassette was now under transcriptional control of the original tetR-VP16 (tTA) transactivator system (FIG. 12). These plasmids were constructed in a similar manner as that described for pTV3Lq+ and pTV3Lq−, and were used to ultimately compare the efficacy of the alternate transactivators in their ability to be down regulated by tetracycline. Specifically, the 0.8 kbp blunt-ended XhoI/SstII fragment (see above) was cloned in both orientations into pTV3tTaTo-LqhIT2 after the vector was digested with NotI (which released the tetop-hGH-LqhIT2 cassette) and blunt-ended with Klenow. The resulting four transfer plasmids contain tetopp35LqA or tetopp35mLqA in both orientations relative to tTA. These transfer plasmids were designated ptTAlq+, ptTAlq+, ptTAMlq+ and ptTAMlq−.

Recombinant viruses were generated by co-transfecting 1 ug of a specific transfer plasmid and 0.5 ug of BaculoGold™ viral DNA (Pharmingen, San Diego, Calif.) into approximately $1.0\times10^6$ Sf-9 cells using lipofectin (GIBCO/BRL, Gaithersburg, Md.).

Transfection supernatants were collected after 5–7 days post-transfection and used in standard plaque purification protocols. Five to six different plaque isolates were selected from the first plaque assay, each plaque was purified an additional time, and the virus initially amplified by infection of about $1.0\times10^6$ Sf-9 cells in a 35 mm tissue culture dish. The resulting virus stock was used to generate working stocks in 75 $cm^2$ tissue culture flasks. The eight different recombinant viruses produced in this manner are found in Table 1.

TABLE 1

Recombinant viruses expressing LqhIT2 under different transactivators

| Virus | Characteristics |
|---|---|
| 1. vTV3lq+ | Contains tet repressor-HR5 transactivator with the operator/p35/lq cassette in the same 5'-3' orientation. |
| 2. vTV3lq− | Same as (1) but with op/p35/lq in opposite orientation. |
| 3. vTV3Mlq+ | Same as (1) but with a modified p35 promoter with late expression ablated. |
| 4. vTV3Mlq− | Same as (3) but with lq cassette in opposite orientation. |
| 5. vtTAlq+ | Contains the tet repressor-VP16 transactivator (lq cassette in same 5'-3' orientation). |
| 6. vtTAlq− | Same as (5) but with lq cassette in opposite orientation. |
| 7. vtTAMlq+ | Same as (5) but with the modified p35 promoter. |
| 8. vtTAMlq− | Same as (7) but with lq cassette in opposite orientation. |

The in vivo activity of selected isolates from a few of these recombinant viruses was evaluated in feeding assays using 3rd instar *Heliothis virescens* larvae to determine if active toxin was expressed during infection and if so, whether the presence of tetracycline or an analog (such as doxycycline or aureomycin) would increase the $LT_{50}$ of the virus relative to untreated controls. In preliminary studies several different treatments were evaluated to determine whether the antibiotic was efficiently absorbed in the insect midgut and if not, whether ingredients in the diet affected absorption, and whether absorption could be improved by direct injection of antibiotic into the insect or by topical application of the antibiotic. 3rd instar *H. virescens* larvae were allowed to consume a diet plug contaminated with 2000 PIBs of vTV3Mlq+ for 24 h either in the presence or absence of 0.3% doxycycline ("Dc"; Sigma Chemical Co., Cat. No. D9891). After 24 h, individual larvae were transferred to the corresponding uncontaminated diet until 40 h post-infection when larvae were treated in the following manner:

A. maintained on the diet (either 0% or 0.3% Dc);

B. injected with 4 ul of a 0.3% solution of Dc in $H_2O$;

C. maintained on 2% (w/v) agar + or −0.3% Dc; or

D. topical application of 4 uL of 0.3% Dc in acetone.

In treatments A, B, and D, larvae were returned to their corresponding diet after treatment. Insects were scored at various times post-infection for symptoms of paralysis. The results of this assay are summarized in Table 2 and provide evidence suggesting that the $LT_{50}$s of the test virus are affected by Dc and that this effect is dependent on the route by which Dc is introduced into the insect.

TABLE 2

Effects of doxycycline on the $LT_{50}$ of vTV3Mlq+ infected *Heliothis virescens* larvae.

| | TREATMENT | $LT_{50}$ (h) |
|---|---|---|
| A[1] | maintained on 0% diet | 84–92 |
| | injected w/ 0.3% Dc | 92–108 |
| | maintained on agar w/o Dc | 84–92 |
| | topical application of 0.3% Dc | 92–108 |
| B[2] | maintained on 0.3% diet | 92 |
| | injected w/ 0.3% Dc | 116–135 |
| | maintained on agar + 0.3% Dc | 135 |
| | topical application of 0.3% Dc | 108–116 |

[1]insects infected and maintained on 0% Dc diet
[2]insects infected and maintained on 0.3% Dc diet Insects infected with vTV3Mlq+ and maintained in the presence of Dc either by injection or feeding on agar died slower than control insects not exposed to Dc. This effect was especially strong in the agar treatments where the $LT_{50}$ was increased by 45 to 60%.

The in vivo activity of selected vtTAlq+, vtTAMlq−, and vTV3Mlq+ viruses was also determined using diet pill bioassays. Third instar *H. virescens* larvae were fed diet pills (volume of 50 uL) containinated with 2000 PIBs (representing about $20\times LC_{50}$) from vtTAlq+, vtTAMlq−, vTV3Mlq+, CG201, or AcMNPV (C6) for 24 h before those insects that had completely consumed their diet were transferred to untreated diet (soy flour/wheat germ insect medium (Bioserv, Cat. No. 9967)) containing 0.3% (w/v) tetracycline (Sigma, Cat. No.T3258), 0.3% (w/v) doxycycline (Sigma, Cat. No. D9891), or 1% (w/v) aureomycin (Bioserve). The antibiotics were added to the molten diet once the temperature of the diet was below 50° C. The amount of antibiotic used in the diet was selected to maximize exposure to the antibiotic without having an adverse effect on the insects (i.e., stunting). Insects were incubated at 28° C. and scored for symptoms of intoxication/viral infection at various times post-infection and the $LT_{50}$ of each virus was determined for each antibiotic treatment (Table 3) using the VISTAT/TIMEfor Analysis, of Time Response Data program (Boyce Thompson Institute at Cornell University, 1990). CG201 is a recombinant virus expressing LqhIT2 under hr5/ie-1 promoter control without the tetracycline transactivator system.

TABLE 3

$LT_{50}$ of recombinant transactivator viruses exposed to different tetracycline analogs

| Virus | Treatment[1] | $LT_{50}$ (h) |
|---|---|---|
| vtTAlq+.3 | untreated | 78.4 |
| | Aureomycin | 95.0 |
| | Tetracycline | 97.4 |
| | Doxycycline | 88.5 |
| vtTAlq+.4 | untreated | 88.2 |
| | Aureomycin | 99.9 |
| | Tetracycline | 96.9 |
| | Doxycycline | 105.4 |
| vtTAlq+.6 | untreated | 66.6 |
| | Aureomycin | 78.3 |
| | Tetracycline | 87.4 |
| | Doxycycline | 91.6 |
| vtTAMlq−.2 | untreated | 89.5 |
| | Aureomycin | 113.7 |
| | Tetracycline | 117.2 |
| | Doxycycline | 113.8 |
| vTV3Mlq+.1 | untreated | 77.3 |
| | Aureomycin | 85.3 |
| | Tetracycline | 79.3 |
| | Doxycycline | 81.9 |
| vTV3Mlq+.5 | untreated | 76.9 |
| | Aureomycin | 82.3 |
| | Tetracycline | 80.0 |
| | Doxycycline | 75.9 |
| CG201 | untreated | 52.6 |
| | Aureomycin | 59.6 |
| | Tetracycline | 58.4 |
| | Doxycycline | 62.7 |
| AcMNPV (C6) | untreated | 97.2 |
| | Aureomycin | 107.8 |
| | Tetracycline | 104.7 |
| | Doxycycline | 97.5 |

[1]all antibiotic treatments performed at 0.3% (w/v) except Aureomycin (1%)

In general, antibiotic treatments increased the $LT_{50}$s of all viruses; however, the effects of these antibiotics on vtTAlq+ 0.6 and vtTAMlq−0.2 were significantly more dramatic than CG201 and AcMNPV. Specifically, these two viruses exhibited about a 30 to 40% increase in the time to kill in the presence of tetracycline or doxycycline relative to untreated control insects. This difference represented a 2 to 3 fold increase over the difference observed with CG201-infected insects. Other viral isolates of vtTAlq+ exhibited less dramatic increases in $LT_{50}$ values relative to CG201. This variability between isolates of the same recombinant virus is likely a result of subtle differences in the expression of both transactivator and toxin by each isolate and is a normal phenomenon observed by people using the baculovirus expression vector system. For this reason several different plaque isolates for each recombinant were tested. The poorest performing recombinants were those that contain LqhIT2 under transcriptional control of the modified transactivator, tetRIE1A (vTV3Mlq+). The significant decrease in the $LT_{50}$'s of these recombinants relative to wild-type AcMNPV suggests that while the tetRIE1A was able to transactivate LqhIT2 expression, expression was not repressed in the presence of antibiotic. This may be due to unanticipated conformational changes to the tetR portion of the transactivator protein when the VP16 activation domain was replaced with the IE1 activation domain that compromises the ability of the transactivator to interact with tetracycline or an analog.

In summary, the bioassay results with selected AcMNPV recombinants expressing LqhIT2 under control of a tetracycline-sensitive transactivator indicate that the $LT_{50}$ of the recombinant viruses can be extended considerably when infection occurs in the presence of an antibiotic which can interact with the transactivator to reduce/delay expression of an insect-selective toxin.

REFERENCES (1) Carbonell, L. F., Klowden, M. J, Miller, L. K., *J. Virol.* (1985), 56, 153–160.
(2) Carbonell, L. F., Miller, L. K., *Appl. Environ. Microbiol.* (1987), 53, 1412–1417.
(3) Brusca, J., Summers, M., Couch, J., Courtney, L., *Intervirol.* (1986), 26, 207–222.
(4) O'Reilly, D. R., Miller, L. K., Luckow, V. A, (1992), *Baculovirus Expression Vectors: A Laboratory Manual*, W. H. Freeman and Company, New York.
(5) King, L. A., Possee, R. D., (1992), *The Baculovirus Expression System*, Chapman and Hall, London.
(6) Granados, R. R., Lawler, K. A., *Virology* (1981), 108, 297–308.
(7) Vlak, J. M., Rohrmann, G. F., In *Viral Insecticides for Biological Control*, Maramorosch, K., Sherman, K. E., Eds., Academnic Press, New York, N.Y. (1985), 489–542.
(8) O'Reilly, D. R., Miller, L. K., *J. Virol.* (1990), 64, 1321–1328.
(9) O'Reilly, D. R., Miller, L. K., *Science* (1989), 245, 1110–1112.
(10) O'Reilly, D. R., Miller, L. K., *Biotechnol.* (1991), 9, 1086–1089.
(11) Carbonell, L. F., Hodge, M. R., Tomalsk, M. D., Miller, L. K., *Gene* (1988), 73, 409–418.
(12) Merryweather, A. T., Weyer, U., Harris, M. P. G., Hirst, M., Booth, T., Possee, R. D., *J. Gen. Virol.* (1990), 71, 1535–1544.
(13) Martens, J. W. M., Honee, G., Zuidema, D., Van Lent, J. W. M., Visser, B., Vlak, J. M., *Appl. Environ. Microbiol.* (1990), 56, 2764–2770.
(14) Tomalski, M. D., Miller, L. K., *Nature* (1991), 352, 82–85.
(15) Tomalski, M. D., Miller, L. K., *Biotech.* (1992), 10, 545–549.
(16) Maeda, S., Volrath, S. L., Hanzlik, T. N., Harper, S. A., Maddox, D. W., Hammock, B. D., Fowler, E., *Virol.* (1991), 184, 777–780.
(17) Stewart, L. M. D., Hirst, M., Ferber, M. L., Merryweather, A. T., Cayley, P. J., Possee, R. D., *Nature* (1991), 352, 85–88.
(18) McCutchen, B. F., Choudary, P. V., Crenshaw, R., Maddox, D., Kamita, S. G., Palekar, N., Volrath, S., Fowler, E., Hammock, B. D., Maeda, S., *Biotech.* (1991), 9, 848–852.
(19) Caruthers, M., in *Methodology of DNA and RNA Sequencing* (1983), Weissman (ed.), Praeger Publishers, New York, Chapter 1.
(20) Zlotkin, E., *Phytoparasitica* (1991), 19, 177–182.
(21) Walther, D., Zlotkin, E., Rathmayer, E., *J. Insect Physiol.* (1976), 22, pp 1187–1194.
(22) Zlotkin, E. in *Neuropharmacology and Pesticide Action* (1986), Ford, Lunt, Raey & Usherwood (eds.), Ellis Horwood, England, pp 352–383.
(23) Zlotkin, E., Fishman, L., Gordon, D. in *Neurotox'88: Molecular Basis of Drug and Pesticide Action*, (1988), Lunt (ed.) pp 35–47.
(24) Zlotkin, E., Rochat, H., Kupeyan, C., Miranda, F., Lissitzky, S., *Biochimie* (Paris) (1971), 53, pp 1073–1078.

(25) Lester, D., Lazarovici, P., Pelhate, M., Zlotkin, E., *Biochem. Biophys. Acta*. (1982), 701, pp 370–381.
(26) Zlotkin, E., Kaduri, D., Gordon, D., Pelhate, M., Martin, M., Rochat, H., *Arch. Biochem. Biophys.* (1985), 240, pp 877–887.
(27) Zlotkin, E., Eitan, M., Bindokas, V. P., Adams, M. E., Moyer, M., Burkhart, W., Fowler, E., *Biochemistry* (1991), 30, pp 4814–4821.
(28) Zlotkin, E., Gurevitz, M., Fowler, E., Adams, M., *Arch. of Insect Biochem. Physiol.* (1993), 22, pp 55–73.
(29) U.S. Pat. No. 4,745,051.
(30) Ernst, W., Grabherr, R., Katinger, H., *Nuc. Acid Res.* (1994), 22, 2855–2856.
(31) Patent Cooperation Treaty, Publication Number WO 94/28114.
(32) Brinster, R. L., Chen, H. Y., Warren, R., Sarthy, A., Palmiter, R. D., *Nature* (1982) 296, pp 39–42.
(33) Mayo, K. E., Warren, R., Palmiter, R. D., *Cell* (1982) 29, pp 99–108.
(34) Hu, M. C.-T., Davidson, N., *Cell* (1987) 48, pp 555–566.
(35) Brown, M., Figge, J., Hansen, U., Wright, C., Jeang, K-T., Khoury, G., Livingston, D. M., Roberts, T. M., *Cell* (1987) 49, pp 603–612.
(36) Figge, J., Wright, C., Collins, C. J., Roberts, T. M., Livingston, D. M., *Cell* (1988) 52, pp 713–722.
(37) Fuerst, T. R., Feanandez, M. P., Moss, B., *Proc. Natl. Acad. Sci.* (1989) 86, pp 2549–2533.
(38) Deutschle, U., Pepperkok, R., Wang, F., Giordano, T. J., McAllister, W. T., Ansorge, W., Bujard, H., *Proc. Natl. Acad. Sci.* (1989) 86, pp 5400–5405.
(39) Deutschle, U., Hipskind, R. A., Bujard, H., *Science* (1990) 248, pp 480–483.
(40) Labow, M. A., Baim, S. B., Shenk, T., Levine, A. J., *Mol. Cell. Biol.* (1990) 10, pp 3343–3356.
(41) Baim, S. B., Labow, M. A., Levine, A. J., Shenk, T., *Proc. Natl. Acad. Sci.* (1991) 88, pp 5072–5076.
(42) Wyborski & Short, *Nucleic Acids Res.* 19, pp 4647–4653.
(43) Bertrand, K. P., Postle, K., Wray, L. V., Reznikoff, W. S., *Gene* (1983) 23, pp 149–156.
(44) Hillen, W., Schollmeier, K., Gatz, C., *J. Mol. Biol.* (1984) 172, pp 185–201.
(45) Gatz, C., Kaiser, A., Wendenburg, R., *Mol. Gen. Genet.* (1991) 227, pp 229–237.
(46) Wirtz, E., Clayton C., *Science* (1995) 268, 1179–1182.
(47) Gossen, M., Bujard, H., *Proc. Natl. Acad. Sci.* (1992) 89, pp 5547–5551.
(48) W.O. Pub. No. 94/29442.
(49) Mével-Ninio, M., Mariol, M.-C., Gans, M., (1989).
(50) Rubin and Spradling (1983).
(51) Handler et al. (1993).
(52) Presnail, J. K., Hoy M. A., *Proc. Natl. Acad. Sci.* (1992) 89, pp 7732–7736.
(53) Presnail, J. K., Hoy M. A., *Exp. Applied Acarology* (1994) 18, pp 319–330.
(54) Robertson, H. M., *Nature* (1993) 362, 241–245.
(55) Jeyaprakash, A., Hoy, M. A., *Insect Mol. Biol.* (1995) 4, pp 31–39.
(56) ffrench-Constant, R. H., Mortlock, D. P., Shaffer, C. D., MacIntyre, R. J., Roush, R. T., *Proc. Natl. Acad. Sci.* (1991) 88, pp 7209–7213.
(57) ffrench-Constant, Steichen, J. C., Ode, P. J., *Pest. Bio. Phys.* (1993) 46, pp 73–77.
(58) Passarelli, A. L., and L. K. Miller, *J. Virol.* (1993) 67, pp 2149–2158.
(59) Kovacs, G. R, Choi, J., Guarino, L. A., and M. D. Summers, *J. Virol.* (1992). 66, pp 7429–7437.
(60) Nissen, M.S., and P. D. Friesen, *J. Virol.* (1989) 63, pp 493–503.

What is claimed is:

1. A method for the production of insecticidal recombinant baculoviruses comprising:
   (a) constructing a recombinant insect cell having a first chimeric gene comprising a first nucleic acid fragment encoding a first promoter, the first nucleic acid fragment operably linked to a second nucleic acid fragment encoding a regulatory protein which affects gene expression;
   (b) constructing a recombinant baculovirus expression vector having a second chimeric gene comprising a third nucleic acid fragment encoding a second promoter that is affected by the regulatory protein encoded by the second nucleic acid, the third nucleic acid fragment operably linked to a fourth nucleic acid fragment encoding an insecticidal protein;
   (c) introducing the recombinant baculovirus expression vector of step (b) into the recombinant insect cell of step (a);
   (d) maintaining the recombinant insect cell from step (c) in an in vitro cell culture, under conditions that support baculovirus replication wherein expression of the regulatory protein encoded by the second nucleic acid fragment affects expression of the insecticidal protein; and
   (e) collecting progeny viruses.

2. The method of claim 1 wherein the recombinant insect cell from step (c) is maintained in an in vitro cell culture.

3. The insecticidal recombinant baculovirus produced by the method of claim 1.

4. The method of claim 1 wherein in step (a):
   (i) the regulatory protein encoded by the second nucleic acid fragment is a tetracycline transactivator protein;
   (ii) the second promoter encoded by the third nucleic acid fragment comprises one or more tetracycline operator sites operably linked to a minimal promoter;
   (iii) the insecticidal protein encoded by the fourth nucleic acid fragment is an insect-selective neurotoxin;

and wherein, in step (d) the conditions that support baculovirus replication comprise the presence of an effective amount of tetracycline or an analog of tetracycline such that the tetracycline transactivator protein is unable to bind to the tetracycline operator sites comprising the third nucleic acid fragment and thereby is unable to induce gene expression directed by the minimal promoter sequence operably linked to the tetracycline operator sites.

5. A method for the production of insecticidal recombinant baculoviruses comprising:
   (a) constructing a recombinant baculovirus expression vector having (1) a first chimeric gene comprising a first nucleic acid fragment encoding a first promoter, the first nucleic acid fragment operably linked to a second nucleic acid fragment encoding a regulatory protein which affects gene expression and (2) a second chimeric gene comprising a third nucleic acid fragment encoding a second promoter that is affected by the regulatory protein encoded by the second nucleic acid fragment, the third nucleic acid fragment operably linked to a fourth nucleic acid fragment encoding an insecticidal protein;
   (b) introducing the recombinant baculovirus expression vector of step (a) into an insect cell;
   (c) maintaining the insect cell from step (b) either in an in vitro cell culture or within an intact, living insect under conditions that support baculovirus replication wherein expression of the regulatory protein encoded by the second nucleic acid fragment affects expression of the insecticidal protein encoded by the fourth nucleic acid fragment; and
   (d) collecting progeny viruses.

6. The method of claim 5 wherein in step (a):
   (i) the regulatory protein encoded by the second nucleic acid fragment is a tetracycline transactivator protein;
   (ii) the second promoter encoded by the third nucleic acid fragment comprises one or more tetracycline operator sites operably linked to a minimal promoter;
   (iii) the insecticidal protein encoded by the fourth nucleic acid fragment is an insect-selective neurotoxin;
and wherein, in step (c) the conditions that support baculovirus replication comprise the presence of an effective amount of tetracycline or an analog of tetracycline such that the tetracycline transactivator protein is unable to bind to the tetracycline operator sites comprising the third nucleic acid fragment and thereby is unable to induce gene expression directed by the minimal promoter sequence operably linked to the tetracycline operator sites.

7. The method of claim 5 wherein the recombinant insect cell from step (b) is maintained in an in vitro cell culture.

8. The method of claim 5 wherein the recombinant insect cell from step (b) is maintained within an intact, living insect.

9. The insecticidal recombinant baculovirus produced by the method of claim 5.

10. A recombinant baculovirus expression vector having a chimeric gene comprising a first nucleic acid fragment encoding a promoter that is affected by a tetracycline transactivator protein, the first nucleic acid fragment operably linked to a second nucleic acid fragment encoding an insecticidal protein.

11. The recombinant baculovirus expression vector of claim 10 wherein the first nucleic acid fragment comprises one or more tetracycline operator sites operably linked to a minimal promoter.

12. The insecticidal recombinant baculovirus of claim 3 wherein the baculovirus is a nuclear polyhedrosis virus.

13. The insecticidal recombinant baculovirus of claim 3 wherein the baculovirus is a granulosis virus.

14. The insecticidal recombinant baculovirus of claim 3 wherein the baculovirus is occluded.

15. The insecticidal recombinant baculovirus of claim 9 wherein the baculovirus is a nuclear polyhedrosis virus.

16. The insecticidal recombinant baculovirus of claim 9 wherein the baculovirus is a granulosis virus.

17. The insecticidal recombinant baculovirus of claim 9 wherein the baculovirus is occluded.

18. An insecticidal recombinant baculovirus having in its genome a chimeric gene comprising a first nucleic acid fragment comprising at least one tetracycline operator and a minimal promoter, the first nucleic acid fragment operably linked to a second nucleic acid fragment encoding an insecticidal protein.

19. The insecticidal recombinant baculovirus of claim 18 further comprising a second chimeric gene comprising a third nucleic acid fragment encoding a regulatory protein which affects expression of the chimeric gene comprising the first and second nucleic acid fragments.

20. The insecticidal recombinant baculovirus of claim 18 wherein the minimal promoter is the AcMNPV p35 minimal promoter.

21. The insecticidal recombinant baculovirus of claim 18 wherein the minimal promoter is a modified p35 minimal promoter wherein the late RNA start site is eliminated.

22. The insecticidal recombinant baculovirus of claim 18 wherein the insecticidal protein is an insect-selective neurotoxin.

23. The insecticidal recombinant baculovirus of claim 19 wherein the regulatory protein is a transactivator.

24. The insecticidal recombinant baculovirus of claim 23 wherein the transactivator is a tetracycline transactivator protein.

25. The insecticidal recombinant baculovirus of claim 23 wherein the transactivator comprises the tetR gene and the activation domain of the AcMNPV IE-1 gene.

26. The insecticidal recombinant baculovirus of claim 24 wherein the tetracycline transactivator protein is tTA.

27. The insecticidal recombinant baculovirus of claim 22 wherein the insect-selective neurotoxin is LqhIT2.

* * * * *

SEQUENCE LISTING

```
(1) GENERAL INFORMATION:

(iii) NUMBER OF SEQUENCES:  27

(2) INFORMATION FOR SEQ ID NO:1:

(i) SEQUENCE CHARACTERISTICS:
        (A) LENGTH:  8 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:1:

CAGATCTG                                                                 8

(2) INFORMATION FOR SEQ ID NO:2:

(i) SEQUENCE CHARACTERISTICS:
        (A) LENGTH:  407 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:2:
```

```
CTCGAGTTTA CCACTCCCTA TCAGTGATAG AGAAAAGTGA AAGTCGAGTT TACCACTCCC        60

TATCAGTGAT AGAGAAAAGT GAAAGTCGAG TTTACCACTC CCTATCAGTG ATAGAGAAAA       120

GTGAAAGTCG AGTTTACCAC TCCCTATCAG TGATAGAGAA AAGTGAAAGT CGAGTTTACC       180

ACTCCCTATC AGTGATAGAG AAAAGTGAAA GTCGAGTTTA CCACTCCCTA TCAGTGATAG       240

AGAAAAGTGA AAGTCGAGTT TACCACTCCC TATCAGTGAT AGAGAAAAGT GAAAGTCGAG       300

CTCAACAGTG GGAGAGAAGG GGCCAGGGTA TAAAAAGGGC CCACAAGAGA CCAGCTCAAG       360

GATTCCAAGG CCGCGGCCCC GAATTCGAGC TCGGTACCCG GGGATCC                    407
```

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
AGCGGCCGCT                                                              10
```

(2) INFORMATION FOR SEQ ID NO:4:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
ACGATGAATT CGGATCCTAT GAAGATCCTC CTTGCTATTG CCCTTATGCT TAGCACCGTG        60

ATGTGGGTGA GCACC                                                        75
```

(2) INFORMATION FOR SEQ ID NO:5:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GACGGCTACA TCAAACGCCG CGACGGCTGC AAAGTGGCCT GCCTTATCGG C                51
```

(2) INFORMATION FOR SEQ ID NO:6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AACGAGGGCT GCGACAAAGA GTGCAAAGCC TACGGCGGCA GCTACGGCTA C                51
```

(2) INFORMATION FOR SEQ ID NO:7:

(i) SEQUENCE CHARACTERISTICS:
            (A) LENGTH:  51 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:7:

TGCTGGACCT GGGGCCTCGC ATGCTGGTGC GAGGGCCTCC CCGACGACAA A    51

(2) INFORMATION FOR SEQ ID NO:8:

(i) SEQUENCE CHARACTERISTICS:
            (A) LENGTH:  48 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:8:

ACCTGGAAAA GCGAGACCAA CACCTGCGGC TAAGGATCCT CTAGAGTC         48

(2) INFORMATION FOR SEQ ID NO:9:

(i) SEQUENCE CHARACTERISTICS:
            (A) LENGTH:  69 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:9:

CACCCACATC ACGGTGCTAA GCATAAGGGC AATAGCAAGG AGGATCTTCA TAGGATCCGA    60

ATTCATCGT                                                            69

(2) INFORMATION FOR SEQ ID NO:10:

(i) SEQUENCE CHARACTERISTICS:
            (A) LENGTH:  51 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:10:

AAGGCAGGCC ACTTTGCAGC CGTCGCGGCG TTTGATGTAG CCGTCGGTGC T    51

(2) INFORMATION FOR SEQ ID NO:11:

(i) SEQUENCE CHARACTERISTICS:
            (A) LENGTH:  51 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:11:

GTAGCTGCCG CCGTAGGCTT TGCACTCTTT GTCGCAGCCC TCGTTGCCGA T    51

(2) INFORMATION FOR SEQ ID NO:12:

(i) SEQUENCE CHARACTERISTICS:

(A) LENGTH:  51 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:12:

GTCGGGGAGG CCCTCGCACC AGCATGCGAG GCCCCAGGTC CAGCAGTAGC G                51

(2) INFORMATION FOR SEQ ID NO:13:

(i) SEQUENCE CHARACTERISTICS:
        (A) LENGTH:  54 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:13:

GACTCTAGAG GATCCTTAGC CGCAGGTGTT GGTCTCGCTT TTCCAGGTTT TGTC             54

(2) INFORMATION FOR SEQ ID NO:14:

(i) SEQUENCE CHARACTERISTICS:
        (A) LENGTH:  243 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:14:

ATGAAGATCC TCCTTGCTAT TGCCCTTATG CTTAGCACCG TGATGTGGGT GAGCACCGAC        60

GGCTACATCA AACGCCGCGA CGGCTGCAAA GTGGCCTGCC TTATCGGCAA CGAGGGCTGC       120

GACAAAGAGT GCAAGGCCTA CGGCGGCAGC TACGGCTACT GCTGGACCTG GGGCCTCGCA       180

TGCTGGTGCG AGGGCCTCCC CGACGACAAA ACCTGGAAAA GCGAAACCAA CACCTGCGGC       240

TAA                                                                    243

(2) INFORMATION FOR SEQ ID NO:15:

(i) SEQUENCE CHARACTERISTICS:
        (A) LENGTH:  20 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:15:

ATGTCTAGAT TAGATAAAAG                                                   20

(2) INFORMATION FOR SEQ ID NO:16:

(i) SEQUENCE CHARACTERISTICS:
        (A) LENGTH:  26 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:16:

AGATCTGGAC CCACTTTACA TTTAAG                                            26

(2) INFORMATION FOR SEQ ID NO:17:

(i) SEQUENCE CHARACTERISTICS:
        (A) LENGTH: 623 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
ATGTCTAGAT TAGATAAAAG TGATTAACAG CGCATTAGAG CTGCTTAATG AGGTCGGAAT    60
CGAAGGTTTA ACAACCCGTA AACTCGCCCA GAAGCTAGGT GTAGAGCAGC CTACATTGTA   120
TTGGCATGTA AAAAATAAGC GGGCTTTGCT CGACGCCTTA GCCATTGAGA TGTTAGATAG   180
GCACCATACT CACTTTTGCC CTTTAGAAGG GGAAAGCTGG CAAGATTTTT TACGTAATAA   240
CGCTAAAAGT TTTAGATGTG CTTTACTAAG TCATCGCGAT GGAGCAAAAG TACATTTAGG   300
TACACGGCCT ACAGAAAAAC AGTATGAAAC TCTCGAAAAT CAATTAGCCT TTTTATGCCA   360
ACAAGGTTTT TCACTAGAGA ATGCATTATA TGCACTCAGC GCTGTGGGGC ATTTTACTTT   420
AGGTTGCGTA TTGGAAGATC AAGAGCATCA AGTCGCTAAA GAAGAAAGGG AAACACCTAC   480
TACTGATAGT ATGCCGCCAT TATTACGACA AGCTATCGAA TTATTTGATC ACCAAGGTGC   540
AGAGCCAGCC TTCTTATTCG GCCTTGAATT GATCATATGC GGATTAGAAA AACAACTTAA   600
GATGTGAAAG TGGGTCCAGA TCT                                          623
```

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
CGGGATCCAT GACGCAAATT AATTTTAACG                                    30
```

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
CCAGATCTTT AACCTTGTGA ATTGTCCAAG TATTC                              35
```

(2) INFORMATION FOR SEQ ID NO:20:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
CGGGATCCAT GACGCAAATT AATTTTAACG CGTCGTACAC CAGCGCTTCG ACGCCGTCCC    60
```

```
GAGCGTCGTT CGACAACAGC TATTCAGAGT TTTGTGATAA CAACCCAAC GACTATTTAA      120

GTTATTATAA CCATCCCACC CCGGATGGAG CCGACACGGT GATATCTGAC AGCGAGACTG     180

CGGCACGTTC AAACTTTTTG GCAAGCGTCA ACTCGTTAAC TGATAATGAT TTAGTGGAAT    240

GTTTGCTCAA GACCACTGAT AATCTCGAAG AAGCAGTTAG TTCTGCTTAT TATTCGGAAT    300

CCCTTGAGCA GCCTGTTGTG GAGCAACCAT CGCCCAGTTC TGCTTATCAT GCGGAATCTT    360

TTGAGCATTC TGCTGGTGTG AACCAACCAT CGGCAACTGG AACTAAACGG AAGCTGGACG    420

AATACTTGGA CAATTCACAA GGTTAAAGAT ACTGG                               455
```

(2) INFORMATION FOR SEQ ID NO:21:

(i) SEQUENCE CHARACTERISTICS:
        (A) LENGTH: 354 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
                20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
    50                  55                  60

Thr His Phe Cys Pro Leu Gly Glu Ser Trp Gln Asp Phe Leu Arg
65                  70                  75                  80

Asn Asn Ala Lys Ser Phe Arg Cys Ala Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Arg
        195                 200                 205

Ser Met Thr Gln Ile Asn Phe Asn Ala Ser Tyr Thr Ser Ala Ser Thr
    210                 215                 220

Pro Ser Arg Ala Ser Phe Asp Asn Ser Tyr Ser Glu Phe Cys Asp Lys
225                 230                 235                 240

Gln Pro Asn Asp Tyr Leu Ser Tyr Tyr Asn His Pro Thr Pro Asp Gly
                245                 250                 255

Ala Asp Thr Val Ile Ser Asp Ser Glu Thr Ala Ala Arg Ser Asn Phe
            260                 265                 270
```

```
Leu Ala Ser Val Asn Ser Leu Thr Asp Asn Asp Leu Val Glu Cys Leu
            275                 280                 285

Leu Lys Thr Thr Asp Asn Leu Glu Glu Ala Val Ser Ser Ala Tyr Tyr
            290                 295                 300

Ser Glu Ser Leu Glu Gln Pro Val Val Glu Gln Pro Ser Pro Ser Ser
305                 310                 315                 320

Ala Tyr His Ala Glu Ser Phe Glu His Ser Ala Gly Val Asn Gln Pro
                325                 330                 335

Ser Ala Thr Gly Thr Lys Arg Lys Leu Asp Glu Tyr Leu Asp Asn Ser
            340                 345                 350

Gln Gly
```

(2) INFORMATION FOR SEQ ID NO:22:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GGATCCAGAC CATGATAAGA TACATTGATG AGTTTGGACA AACCACAACT AGAATGCAGT    60

GAAAAAAATG CTTTATTTGT GAAATTTGTG ATGCTATTGC TTTATTTGTA ACCATTATAA   120

GCTGCAATAA ACAAGTTAAC AACAACAATT GCATTCATTT TATGTTTCAG GTTCATTTTT   180

AGGTGTGGGA GGTTTTTTCG GATCC                                        205
```

(2) INFORMATION FOR SEQ ID NO:23:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
CTATAAATAT TCAACGTTGC TTGTATTAAG TGAGCATTTG AGCTTTACCA AGGATCCGCG    60

GCCGCAGCT                                                           69
```

(2) INFORMATION FOR SEQ ID NO:24:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
GCGGCCGCGG ATCCTTGGTA AAGCTCAAAT GCTCACTTAA TACAAGCAAC GTTGAATATT    60

TATAGAGCT                                                           69
```

(2) INFORMATION FOR SEQ ID NO:25:

(i) SEQUENCE CHARACTERISTICS:
        (A) LENGTH: 69 base pairs
        (B) TYPE: nucleic acid
        (C) STRANDEDNESS: single

```
              (D) TOPOLOGY: linear (ii) MOLECULE TYPE: DNA (genomic)

(xi) SEQUENCE DESCRIPTION: SEQ ID NO:25:

CTATAAATAT TCAACGTTGC TTGTATTCAG TGAGCATTTG AGCTTTACCA AGGATCCGCG    60

GCCGCAGCT                                                            69

(2) INFORMATION FOR SEQ ID NO:26:

(i) SEQUENCE CHARACTERISTICS:
              (A) LENGTH: 69 base pairs
              (B) TYPE: nucleic acid
              (C) STRANDEDNESS: single
              (D) TOPOLOGY: linear (ii) MOLECULE TYPE: DNA (genomic)

(xi) SEQUENCE DESCRIPTION: SEQ ID NO:26:

GCGGCCGCGG ATCCTTGGTA AAGCTCAAAT GCTCACTGAA TACAAGCAAC GTTGAATATT    60

GCCGCAGCT                                                            69

(2) INFORMATION FOR SEQ ID NO:27:

(i) SEQUENCE CHARACTERISTICS:
              (A) LENGTH: 80 amino acids
              (B) TYPE: amino acid
              (C) STRANDEDNESS: single
              (D) TOPOLOGY: linear (ii) MOLECULE TYPE: protein (xi) SEQUENCE DESCRIPTION: SEQ ID NO:27:

Met Lys Ile Leu Leu Ala Ile Ala Leu Met Leu Ser Thr Val Met Trp
 1               5                  10                  15

Val Ser Thr Asp Gly Tyr Ile Lys Arg Arg Asp Gly Cys Lys Val Ala
            20                  25                  30

Cys Leu Ile Gly Asn Glu Gly Cys Asp Lys Glu Cys Lys Ala Tyr Gly
            35                  40                  45

Gly Ser Tyr Gly Tyr Cys Trp Thr Trp Gly Leu Ala Cys Trp Cys Glu
        50                  55                  60

Gly Leu Pro Asp Asp Lys Thr Trp Lys Ser Glu Thr Asn Thr Cys Gly
65                  70                  75                  80
```